United States Patent
Pagani

(10) Patent No.: US 9,008,785 B2
(45) Date of Patent: Apr. 14, 2015

(54) RETINAL PROSTHESIS

(75) Inventor: Alberto Pagani, Nova Milanese (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 13/977,121

(22) PCT Filed: Dec. 30, 2011

(86) PCT No.: PCT/IB2011/056033
§ 371 (c)(1),
(2), (4) Date: Jul. 12, 2013

(87) PCT Pub. No.: WO2012/090188
PCT Pub. Date: Jul. 5, 2012

(65) Prior Publication Data
US 2013/0282119 A1    Oct. 24, 2013

(30) Foreign Application Priority Data

Dec. 30, 2010 (IT) ............................. TO2010A1095
Jan. 31, 2011 (IT) ............................. TO2011A0078

(51) Int. Cl.
A61F 2/14       (2006.01)
A61F 9/08       (2006.01)
(Continued)

(52) U.S. Cl.
CPC ... *A61F 2/14* (2013.01); *A61F 9/08* (2013.01); *A61N 1/0543* (2013.01); *A61N 1/36046* (2013.01)

(58) Field of Classification Search
USPC ..................................................... 607/53, 54
See application file for complete search history.

(56) References Cited

U.S. PATENT DOCUMENTS 4,628,933 A    12/1986   Michelson
5,109,844 A     5/1992   de Juan, Jr. et al.
(Continued)

FOREIGN PATENT DOCUMENTS

WO      WO 0183026 A1     11/2001
WO      WO 2010124321 A1 * 11/2010  ............. A61N 1/378

OTHER PUBLICATIONS

Abrial, Andre et al: "A New Contactless Smart Card IC Using an On-Chip Antenna and an Asynchronous Microcontroller," IEEE Journal of Solid-State Circuits, vol. 36, No. 7, Jul. 2001 (pp. 1101-1107).
(Continued)

*Primary Examiner* — Carl H Layno
*Assistant Examiner* — Erin Piateski
(74) *Attorney, Agent, or Firm* — Gardere Wynne Sewell LLP

(57) ABSTRACT

A retinal prosthesis including an electronic stimulation unit housed inside an eye and including: a plurality of electrodes that contact a portion of a retina of the eye; an electronic control circuit, which is electrically connected to the electrodes and supplies to the electrodes electrical stimulation signals designed to stimulate the portion of retina; and a local antenna connected to the electronic control circuit. The retinal prosthesis further includes an electromagnetic expansion housed inside the eye and formed by a first expansion antenna and a second expansion antenna electrically connected together, the first expansion antenna being magnetically or electromagnetically coupled to an external antenna, the second expansion antenna being magnetically or electromagnetically couple to the local antenna, the electromagnetic expansion moreover receiving an electromagnetic supply signal transmitted by the external antenna and generating a corresponding replica signal.

20 Claims, 18 Drawing Sheets

(51) Int. Cl.
*A61N 1/05* (2006.01)
*A61N 1/36* (2006.01)

(56) References Cited

U.S. PATENT DOCUMENTS

| | | | |
|---|---|---|---|
| 5,935,155 | A | 8/1999 | Humayun et al. |
| 6,298,270 | B1 | 10/2001 | Nisch et al. |
| 6,324,429 | B1 | 11/2001 | Shire et al. |
| 6,427,087 | B1 | 7/2002 | Chow et al. |
| 6,976,998 | B2 | 12/2005 | Rizzo et al. |
| 7,047,080 | B2 | 5/2006 | Palanker et al. |
| 7,103,416 | B2 | 9/2006 | Ok et al. |
| 7,263,403 | B2 | 8/2007 | Greenberg et al. |
| 7,265,402 | B2 | 9/2007 | Koyanagi |
| 7,483,750 | B2 | 1/2009 | Greenberg et al. |
| 2003/0093131 | A1* | 5/2003 | Loeb et al. ............ 607/48 |
| 2003/0097165 | A1* | 5/2003 | Krulevitch et al. ........ 607/115 |
| 2004/0186533 | A1* | 9/2004 | Greenberg et al. ......... 607/54 |
| 2006/0106432 | A1* | 5/2006 | Sawan et al. ............ 607/54 |
| 2006/0282128 | A1 | 12/2006 | Tai et al. |
| 2008/0046033 | A1 | 2/2008 | McClure et al. |
| 2008/0090322 | A1* | 4/2008 | Mech et al. ............... 438/64 |
| 2008/0308928 | A1 | 12/2008 | Chang et al. |
| 2009/0033467 | A1* | 2/2009 | Finocchiaro et al. ........ 340/10.1 |
| 2010/0312310 | A1* | 12/2010 | Meskens ................. 607/61 |
| 2012/0116507 | A1* | 5/2012 | Ng et al. ................. 623/6.63 |

OTHER PUBLICATIONS

Guo, L.H. et al: "Design and Manufacturing of Small Area On-Chip-Antenna (OCA) for RFID Tags," IEEE, 2006 (pp. 198-201).

Shire, Douglas B., et al: "Development and Implantation of a Minimally-Invasive Wireless Sub-Retinal Neurostimulator," IEEE 2009 (pp. 1-11).

International Search Report dated Mar. 16, 2012 from corresponding PCT Application No. PCT/IB2011/056033.

Watanabe, T. et al., "Novel Retinal Prosthesis System with Three Dimensionally Stacked LSI Chip," European Solid-State Device Research Conference, 2006.

\* cited by examiner

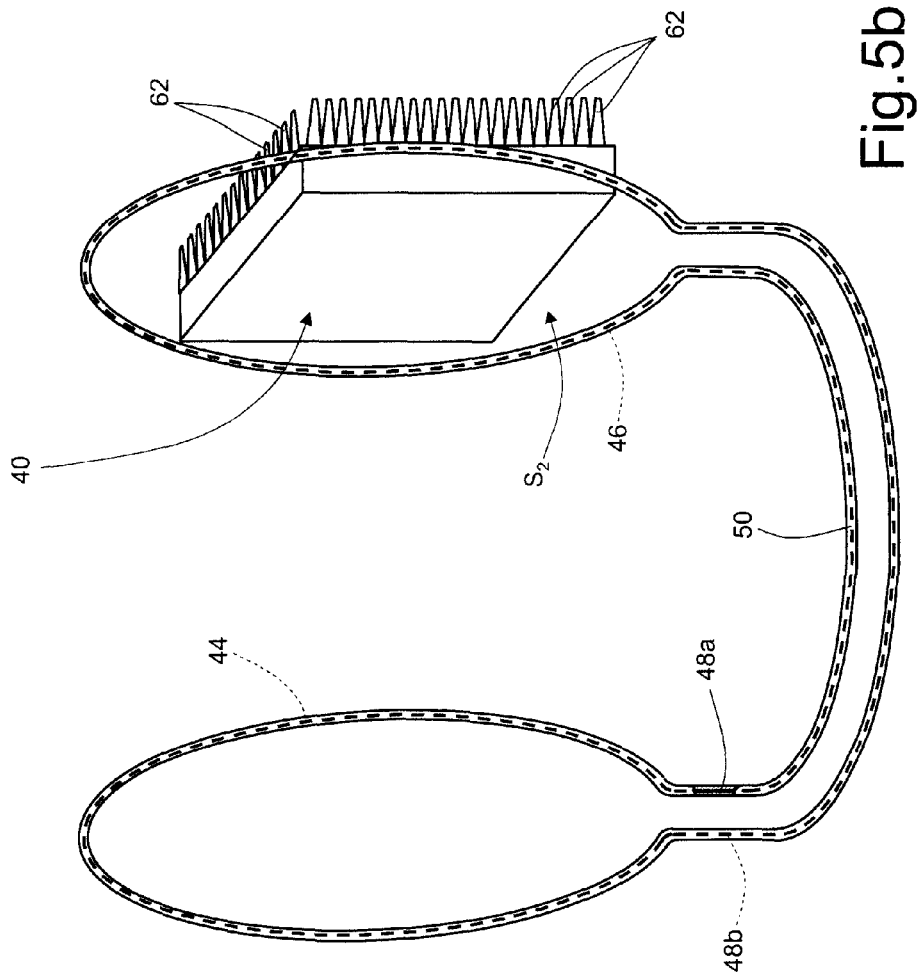
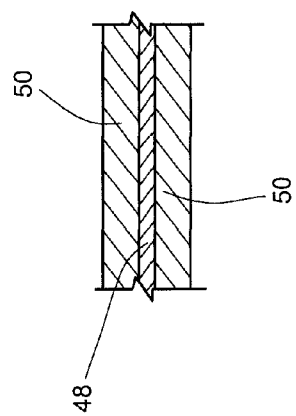

RETINAL PROSTHESIS

CROSS REFERENCE TO RELATED APPLICATIONS

This application is a U.S. National Stage patent application based on International patent application number PCT/IB2011/056033 filed Dec. 30, 2011, which claims the priority benefit of Italian patent application numbers TO2010A001095, filed Dec. 30, 2010, and TO2011A000078, filed Jan. 31, 2011, and which applications are hereby incorporated by reference to the maximum extent allowable by law.

BACKGROUND

1. Technical Field

The present disclosure relates to a retinal prosthesis.

2. Discussion of the Related Art

As is known, there are now available numerous retinal prostheses, which are electronic systems with medical purposes, designed for persons having visual impairments.

In general, a retinal prosthesis performs the function of making up, at least in part, for a reduced functionality of the retina, caused by a pathological condition of the retina itself, such as, for example, retinitis pigmentosa.

In greater detail, retinal prostheses are divided into retinal prostheses of an epiretinal type and retinal prostheses of a subretinal type. In use, prostheses of an epiretinal type are arranged, at least in part, on the surface of the retina that is exposed to the light, hence on the surface of the retina facing the crystalline lens. Instead, prostheses of a subretinal type are arranged, at least in part, between the retina and the so-called retinal pigment epithelium, which is the layer of pigment cells that is located on the outside of the retina itself.

This said, irrespective of the type, retinal prostheses each comprise a respective internal unit and a respective external unit. In use, the external unit is set externally with respect to the eye, whereas the internal unit is set inside the eye, and in particular within the vitreous body.

By way of example, FIG. 1a shows a retinal prosthesis 1, the external and internal units of which are designated, respectively, by 2 and 4.

The external unit 2 comprises a transmitter 6 and a first antenna 8, which is electrically connected to the transmitter 6 and is formed, for example, by a coil made of conductive material.

The internal unit 4 comprises a second antenna 10, which is also formed, for example, by a coil of conductive material. Furthermore, the internal unit 4 comprises an integrated electronic device 12 and an electrical connection cable 14, which connects the second antenna 10 to the integrated electronic device 12; for example, the electrical connection cable 14 can be a flexible electrical bus.

The integrated electronic device 12 functions as artificial retina and comprises a plurality of photodetectors 18 (FIG. 1b), an electronic circuitry 19 (FIG. 2), and a plurality of electrodes 20 (FIG. 1b).

As shown in greater detail in FIG. 1b, the integrated electronic device 12 has substantially the shape of a parallelepiped and has a bottom surface 12a and a top surface 12b. The photodetectors 18 face the top surface 12b so as that they can be reached by the light coming from the outside world, whilst the electrodes 20 extend underneath the bottom surface 12a. In turn, the bottom surface 12a is constrained, for example by means of an appropriate adhesive layer (not shown), to the electrical connection cable 14, which, in practice, carries the integrated electronic device 12.

As shown in greater detail in FIG. 2, the electronic circuitry 19 is electrically connected to the photodetectors 18 and to the electrodes 20. Furthermore, the electrical connection cable 14 comprises at least a first conductive element 14a and a second conductive element 14b, and an insulating sheath 14c, which envelops the first and second conductive elements 14a, 14b and carries the integrated electronic device 12. The first and second conductive elements 14a, 14b are electrically connected to the electronic circuitry 19, for example by means of a first via 21a and a second via 21b, respectively. In addition, the first and second conductive elements 14a, 14b are electrically connected, respectively, to a first terminal and a second terminal of the second antenna 10. Furthermore, the first and second conductive elements 14a, 14b, the insulating sheath 14c, and the electrodes 20 are such that the electrodes 20 themselves traverse the electrical connection cable 14 without contacting electrically the first and second conductive elements 14a, 14b, but rather contacting just the insulating sheath 14c. Moreover, the electrodes 20 extend through the adhesive layer set between the bottom surface 12a and the insulating sheath 14c, if this is present.

As previously mentioned, and as shown in FIG. 1a, in use the external unit 2 is set in the proximity of the eye, inside which the internal unit 4 is located. For example, the external unit 2 can be mounted on a pair of glasses, in such a way that the first antenna 8 is arranged within a lens of the pair of glasses, and in particular is arranged along the edge of said lens so as to enable the light to penetrate the eye. The transmitter 6 can be carried by an arm of the glasses.

The internal unit 4 is set inside the eye in such a way that the second antenna 10 is arranged in the proximity of the crystalline lens, possibly surrounding part of the crystalline lens itself.

The integrated electronic device 12 is arranged in the proximity of the retina of the eye, and in particular is arranged in such a way that the electrodes 20 will contact a portion of retina traversed by the optical axis of the crystalline lens, opposite to the pupil and including the so-called macula. Finally, the electrical connection cable 14 is arranged so as to pass along the inner wall of the bulb of the eye, without crossing the optical axis of the crystalline lens.

In greater detail, the second antenna 10 is arranged so as not to obstruct the path of the light rays that traverse the crystalline lens, and hence so as to enable the light that penetrates through the crystalline lens to reach the retina. Consequently, the second antenna 10 is arranged so as to surround the optical axis of the crystalline lens. In practice, in the case where the second antenna 10 is formed by a coil of conductive material, the axis of said coil coincides, to a first approximation, with the optical axis of the crystalline lens, which, amongst other things, intercepts the integrated electronic device 12.

In this way, the light coming from the outside world traverses the crystalline lens without undergoing significant alterations on account of the presence of the second antenna 10, and impinges on the integrated electronic device 12, and in particular on the photodetectors 18, which generate corresponding electrical signals, which in turn are supplied to the electronic circuitry 19. On the basis of the electrical signals supplied by the photodetectors 18, the electronic circuitry 19 generates, on the electrodes 20, corresponding electrical stimulation signals, which stimulate electrically the portion of retina in contact with the electrodes 20. In particular, the electrodes 20 stimulate the so-called internal retina (designated by 22 in FIG. 1b), which is formed, amongst other things, by the ganglion cells, the axons of which form the optical nerve. In this way, the retinal prosthesis 1 makes up, at least in part, for a possible reduced functionality of the so-called photoreceptor cells (designated by 24 in FIG. 1b), which include the cones and rods. In fact, since the ganglion cells are arranged between the photoreceptor cells 24 and the electrodes 20, the electrical stimulation signals do not traverse the photoreceptor cells 24, but rather directly stimulate the optical nerve.

In order to supply the integrated electronic device 12, the transmitter 6 generates a supply signal of an electromagnetic type, which is irradiated by the first antenna 8 and received by the second antenna 10 in such a way that, after prior propagation along the electrical connection cable 14, the supply signal reaches the integrated electronic device 12, supplying thereto the power necessary for its operation.

In greater detail, according to the frequency of the supply signal and to the distance between the first and second antennas 8, 10 a coupling of a magnetic or electromagnetic type is formed in such a way that a transfer of electric power occurs from the first antenna 8 to the second antenna 10. The electric power present on the second antenna 10 is then transferred to the integrated electronic device 12. In greater detail, in the particular case of magnetic coupling, the first and second antennas 8, 10 function as primary and secondary of a transformer.

Retinal prostheses similar to the retinal prosthesis 1, hence of an epiretinal type, are described, by way of example, in "Novel Retinal Prosthesis System with Three Dimensionally Stacked LSI Chip", European Solid-State Device Research Conference, 2006, by Watanabe T. et al., or else in U.S. Pat. No. 6,976,998.

In general, retinal prostheses are known in which, instead of the integrated electronic device 12, a so-called system in package (SiP) is present, or else a stack of integrated circuits, also known as three-dimensional integrated circuit (3D IC). In addition, the electrodes 20 can form an array of electrodes structurally separate from the integrated electronic device 12.

Furthermore, retinal prostheses are known of the type described in US20060282128, where the external unit comprises a system for acquisition and processing of images, which are transmitted to the internal unit by means of coupling between the first antenna and the second antenna. In this case, the integrated electronic device may not comprise any photodetector.

Likewise known are retinal prostheses, and more precisely subretinal prostheses, of the type described in U.S. Pat. No. 7,483,750, where the electrodes are arranged between the internal retina and the external retina.

Once again with reference to the retinal prosthesis 1, this makes possible, after implant, to make up at least in part for a reduced functionality of the photoreceptor cells 24. However, in the case where the integrated electronic device 12 undergoes damage and has to be replaced, it becomes necessary to extract from the eye the entire internal unit 4.

SUMMARY

Embodiments provide a retinal prosthesis that will enable the drawbacks of the known art to be at least partially overcome.

According to one embodiment, there is provided a retinal prosthesis comprising an electronic stimulation unit, which is configured for being housed inside an eye and includes a plurality of electrodes, configured for contacting a portion of a retina of the eye; an electronic control circuit, which is electrically connected to said electrodes and is configured for supplying to the electrodes electrical stimulation signals designed to stimulate said portion of retina; a local antenna connected to the electronic control circuit; and an electromagnetic expansion, which is configured for being housed inside the eye and is formed by a first expansion antenna and a second expansion antenna electrically connected together, the first expansion antenna being configured for being coupled magnetically or electromagnetically to an external antenna, the second expansion antenna being configured for being coupled magnetically or electromagnetically to said local antenna, the electromagnetic expansion being further configured for receiving an electromagnetic supply signal transmitted by said external antenna and generating a corresponding replica signal.

According to an embodiment, the electronic control circuit comprises a supply stage connected to the local antenna and configured for generating, following upon reception of the replica signal, a converted signal designed to supply the electronic control circuit.

According to an embodiment, said supply stage comprises an AC/DC converter.

According to an embodiment, the electromagnetic expansion is configured for resonating following upon reception of the electromagnetic supply signal.

According to an embodiment, the electromagnetic expansion further comprises an electrical network including at least one between a reactive element and a matching network configured for matching the impedances of the first and second expansion antennas.

According to an embodiment, the electromagnetic expansion comprises at least one arm hinged to the second expansion antenna about a first axis of rotation.

According to an embodiment, the electromagnetic expansion is elastically displaceable between a resting state, where the arm is straight, and an operative state, where the arm substantially assumes, at least locally, a radius of curvature of an inner wall of the eye.

According to an embodiment, the arm is moreover hinged to the first expansion antenna about a second axis of rotation, and the electromagnetic expansion is elastically displaceable between a resting state, in which the first and second axes of rotation are distinct, and an operative state, in which the first and second axes of rotation coincide.

According to an embodiment, the electronic stimulation unit comprises a dielectric region, a first connection region housing first conductive connection lines, and a first body of semiconductor material, the first body being arranged between, and in direct contact with, the dielectric region and the first connection region, the electronic control circuit being formed at least in part inside the first body; and wherein the local antenna is housed inside the dielectric region and is connected to the electronic control circuit by means of the first conductive connection lines and by means of a pair of conductive elements that extend through the first body.

According to an embodiment, the electronic stimulation unit comprises a first connection region housing first conductive connection lines, and a first body of semiconductor material contiguous to the first connection region, the electronic control circuit being formed at least in part inside the first body; and wherein the local antenna is housed inside the first connection region and is connected to the electronic control circuit by means of the first conductive connection lines.

According to an embodiment, the electronic stimulation unit comprises a first integrated circuit and a second integrated circuit, the first integrated circuit comprising a first body of semiconductor material, a first connection region, which is contiguous to the first body and houses first conductive connection lines, and a passivation region, which is contiguous to the first connection region; the second integrated circuit comprising a second body of semiconductor material and a second connection region, which is contiguous to the second body and houses second conductive connection lines, the first and second integrated circuits being connected by interposition of an insulating region contiguous to the first body and to the second connection region; the electronic stimulation unit further comprising a dielectric region contiguous to the passivation region; and wherein the electronic control circuit comprises a first electronic circuitry, formed at least in part inside the first body, and a second electronic circuitry, formed at least in part inside the second body, the first and second electronic circuitries being electrically connected by means of at least one metal via, which extends through the first body and the insulating region; and wherein the local antenna is housed inside the dielectric region and is electrically connected to the first electronic circuitry.

According to an embodiment, the electronic stimulation unit comprises a first integrated circuit and a second integrated circuit, the first integrated circuit comprising a first body of semiconductor material, a first connection region contiguous to the first body and housing first conductive connection lines, and a passivation region contiguous to the first connection region; the second integrated circuit comprising a second body of semiconductor material and a second connection region, which is contiguous to the second body and houses second conductive connection lines, the first and second integrated circuits being connected by interposition of an insulating region, contiguous to the first body and to the second connection region; and wherein the electronic control circuit comprises a first electronic circuitry, formed at least in part inside the first body, and a second electronic circuitry, formed at least in part inside the second body, the first and second electronic circuitries being electrically connected by means of at least one metal via extending through the first body and the insulating region; and wherein the local antenna is housed inside the first connection region and is electrically connected to the first electronic circuitry.

According to an embodiment, the electronic stimulation unit further comprises a layer of polymeric material, the electrodes being formed partially within the layer of polymeric material.

According to an embodiment, the electronic stimulation unit further comprises a package of insulating material, which encloses the electronic control circuit and the local antenna, the electrodes extending at least in part outside the package.

According to an embodiment, the electronic stimulation unit comprises a magnet configured for constraining the electronic stimulation unit to the electromagnetic expansion.

According to an embodiment, the retinal prosthesis comprises an external unit including said external antenna, an external transceiver connected to the external antenna, and an image-acquisition device connected to the external transceiver; and wherein the electronic control circuit comprises an internal transceiver, connected to the local antenna.

According to an embodiment, the first and second expansion antennas are spiral antennas, and wherein the electronic stimulation unit is surrounded at least in part by the second expansion antenna.

BRIEF DESCRIPTION OF THE DRAWINGS

For a better understanding of the embodiments, which are now described, purely by way of non-limiting example and with reference to the attached drawings,
wherein:

FIG. 1b is a schematic illustration of a portion of the retinal prosthesis shown in FIG. 1a;

FIG. 2 is a schematic illustration of a cross section of a portion of the retinal prosthesis shown in FIG. 1a;

FIG. 5a shows a cross section of a portion of an electromagnetic expansion;

FIG. 5b is a schematic illustration of a view of a portion of the retinal prosthesis shown in FIG. 3;

DETAILED DESCRIPTION

Figure 1A:
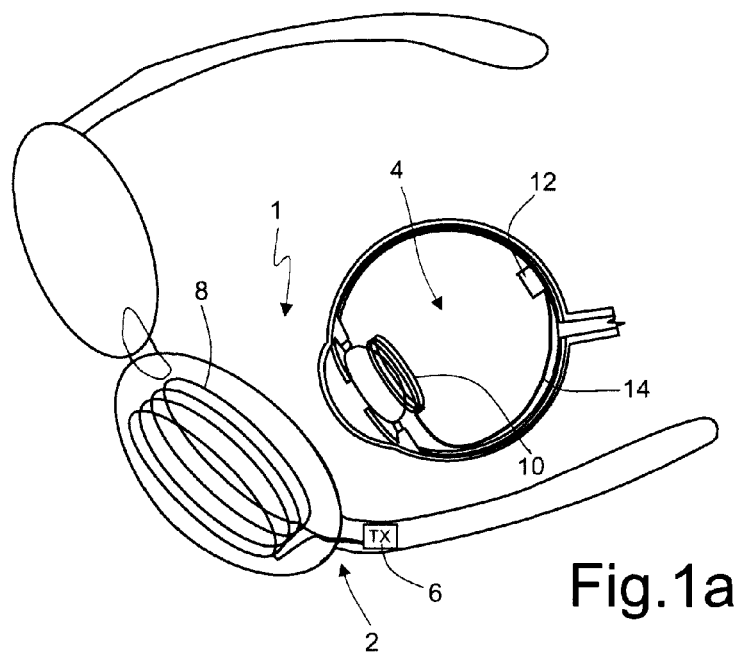
FIG. 1a is a schematic illustration of a retinal prosthesis of a known type.
Figure 1B:
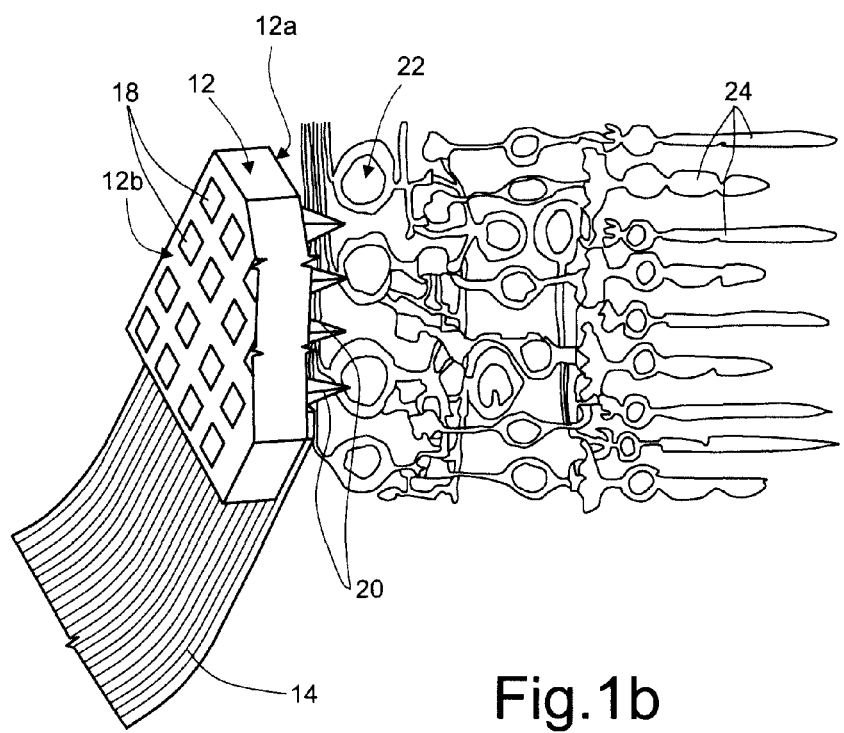
Figure 2:
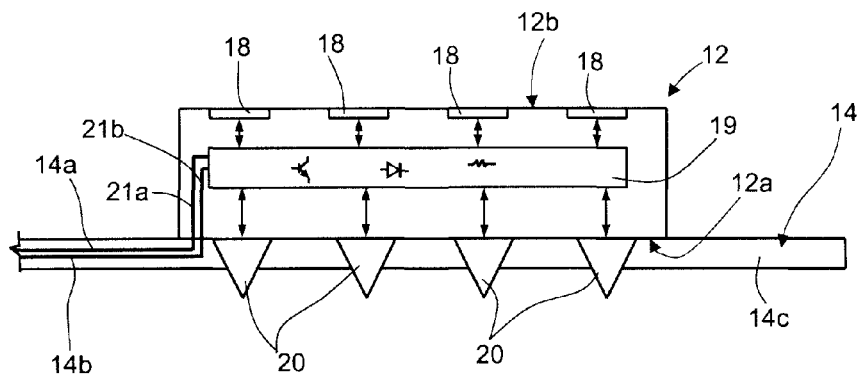
Figure 3:
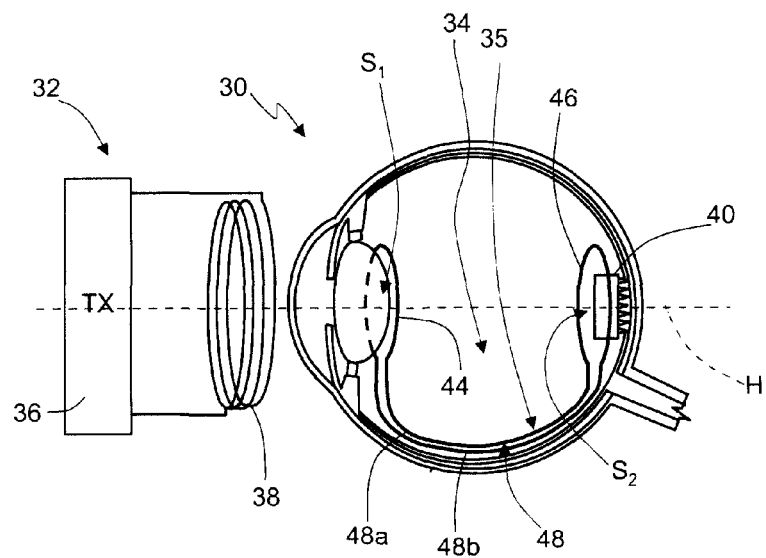
FIG. 3 is a schematic illustration of a retinal prosthesis according to the present invention.

FIG. 3 shows a retinal prosthesis 30, which comprises an external unit 32 and an internal unit 34.

The external unit 32 comprises a transmitter 36 and an external antenna 38, which is electrically connected to the transmitter 36 and is formed, for example, by a coil of conductive material.

The internal unit 34 comprises an electromagnetic expansion 35 and a stimulating unit 40.

In greater detail, the electromagnetic expansion 35 is formed by a first expansion antenna 44, a second expansion antenna 46, and an electrical network 48, which electrically connects the first and second expansion antennas 44, 46.

The first and second expansion antennas 44, 46 may be spiral antennas; for example, in the embodiment illustrated in FIG. 3, the first and second expansion antennas 44, 46 are formed, each, by a respective loop of conductive material. In particular, the loop forming the first expansion antenna 44 has a diameter $D_{44}$, while the loop forming the second expansion antenna 46 has a diameter $D_{46}$.

More in particular, the first and second expansion antennas 44, 46 are arranged, respectively, in the proximity of the crystalline lens and in the proximity of a portion of retina facing the crystalline lens itself, traversed by the optical axis of the crystalline lens (designated by H) and opposite to the pupil, it being possible for this portion of retina to include the so-called macula. In what follows, for simplicity the aforementioned portion of retina will be referred to as "portion of retina to be stimulated".

Even more in particular, the first and second expansion antennas 44, 46 may be arranged in such a way that the axes of the respective loops substantially coincide with the optical axis H of the crystalline lens. Furthermore, the dimensions of the loops of the first and second expansion antennas 44, 46, as well as the diameters $D_{44}$ and $D_{46}$, are such that, on the hypothesis of light rays coming from infinity, these light rays can traverse the first and second expansion antennas 44, 46 without interfering with them. In fact, after traversing the crystalline lens, the light rays can traverse a first portion of space $S_1$, delimited by the loop forming the first expansion antenna 44, and then a second portion of space $S_2$, delimited by the loop forming the second expansion antenna 46, without being reflected either by the first expansion antenna 44 or by the second expansion antenna 46.

As shown in FIG. 3, the electrical network 48 may be formed by two wires of conductive material (designated by 48a and 48b), which connect, respectively, a first terminal of the first expansion antenna 44 to a first terminal of the second expansion antenna 46, and a second terminal of the first expansion antenna 44 to a second terminal of the second expansion antenna 46.

Figure 4A:
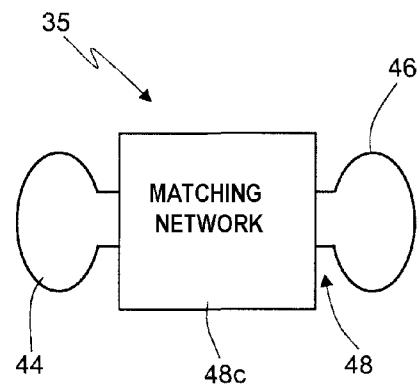
FIGS. 4a and 4b are schematic illustrations of electromagnetic expansions.

As described in US2009-0033467 A1, the electrical network 48 may comprise, instead of the wires of conductive material or else in addition to them, an impedance-matching network 48c (FIG. 4a) designed to match the impedance that the first expansion antenna 44 presents in regard to the second antenna 46, and vice versa. In practice, the impedance-matching network 48c causes, at a certain design frequency, the impedance of the second expansion antenna 46 seen by the first expansion antenna 44 to be equal to the complex conjugate of the impedance of said first expansion antenna 44, and vice versa.

Figure 4B:
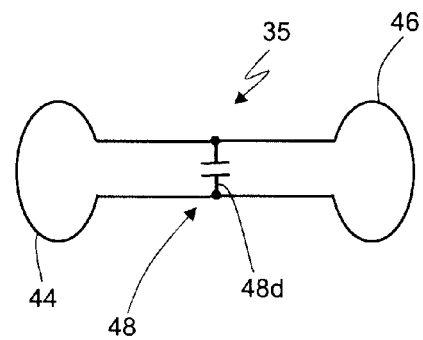

Alternatively, the electrical network 48 may comprise a reactive element such that the electromagnetic expansion 35 functions as series or parallel resonator. In particular, in the case of the parallel resonator, the reactive element is chosen in such a way that the imaginary part of the admittance of the electromagnetic expansion 35 is substantially zero, whereas, in the case of the series resonator, the reactive element is chosen in such a way that the imaginary part of the impedance of the electromagnetic expansion 35 is substantially zero. For example, as shown in FIG. 4b, the reactive element may be formed by a capacitor 48d in such a way that, since the electrical behavior of the first and second expansion antennas 44, 46 is of an inductive type, the electromagnetic expansion 35 can resonate at a resonance frequency, which can be determined in a way in itself known.

Irrespective of the above details of implementation, the electromagnetic expansion 35 is passive and comprises a protective coating 50 (FIGS. 5a and 5b), made of insulating material such as, for example, parylene. In particular, the protective coating 50 coats the first and second expansion antennas 44, 46, and the electrical network 48. In addition, the protective coating 50, the first and second antennas 44, 46, and possibly also the electrical network 48 (in particular, in the case where it is formed by two wires of conductive material), may be such as to bestow flexibility on the electromagnetic expansion 35, as described in greater detail hereinafter.

As shown in greater detail in FIG. 5b, in use the stimulating unit 40 may be arranged at least in part within the second portion of space $S_2$ so as to be surrounded at least in part by the second expansion antenna 46. Furthermore, the stimulating unit 40 has a plurality of electrodes 62, which can contact the portion of retina to be stimulated.

Figure 6:
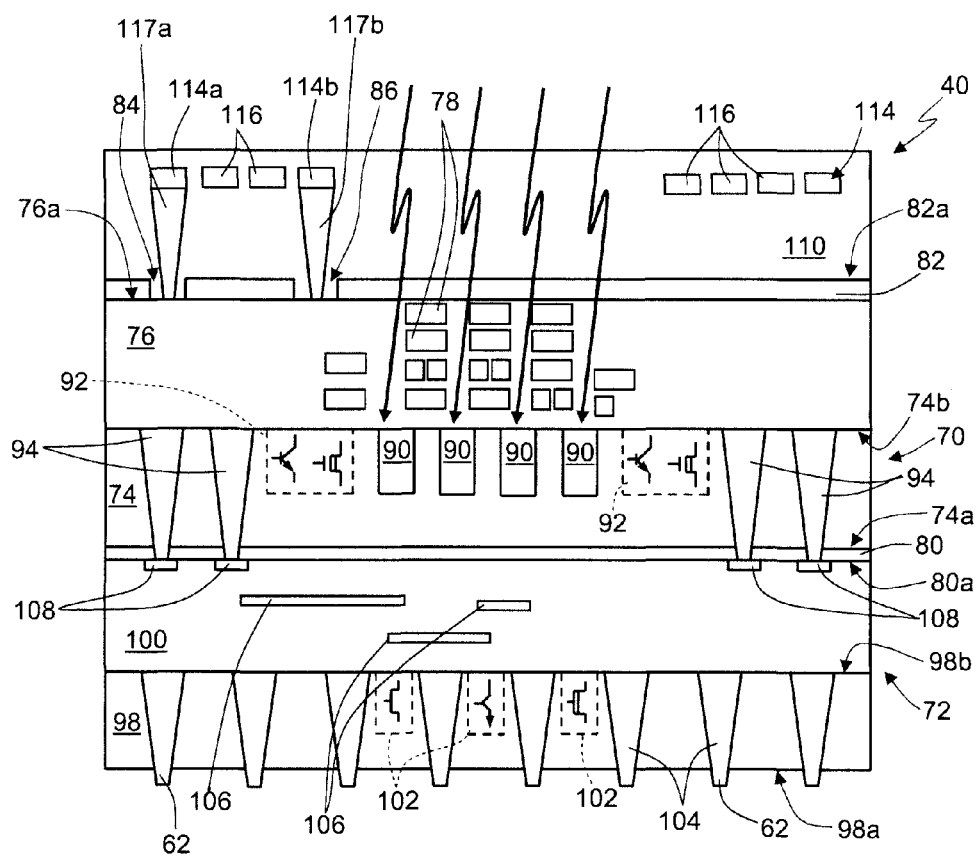
FIGS. 6, 8, 9, 11, 12, 15, 16 and 17 are schematic illustrations of sections of variants of a stimulating unit.

As shown in detail in FIG. 6, the stimulating unit 40 is formed by a first integrated circuit or chip 70 and by a second integrated circuit or chip 72, arranged on top of one another. In particular, the first chip 70 is arranged on top of the second chip 72.

It should be noted that, in describing the stimulating unit 40, except where otherwise specified, the terms "overlying", "underlying", "bottom", "top", etc. refer to the stimulating unit as shown in the figures themselves, i.e., irrespective of the effective arrangement that the stimulating unit will assume in use.

This being said, the first chip 70 comprises a first body 74 of semiconductor material, delimited at the bottom by a first surface 74a and delimited at the top by a second surface 74b. Furthermore, the first chip 70 comprises a first connection region 76, which extends above the second surface 74b, in direct contact with the first body 74. The first connection region 76 is delimited at the top by a third surface 76a and may comprise one or more dielectric layers (not shown), as well as one or more metal connection lines 78, which will be referred to hereinafter as "first connection lines 78".

Extending underneath the first body 74, and in direct contact with the first surface 74a, is a first insulating region 80, delimited at the bottom by a fourth surface 80a. Furthermore, extending above the third surface 76a, and in direct contact with the first connection region 76, is a passivation region 82, which is made of insulating material, is delimited at the top by a fifth surface 82a, and defines at least one first window 84 and one second window 86, described in detail hereinafter.

Figure 7:
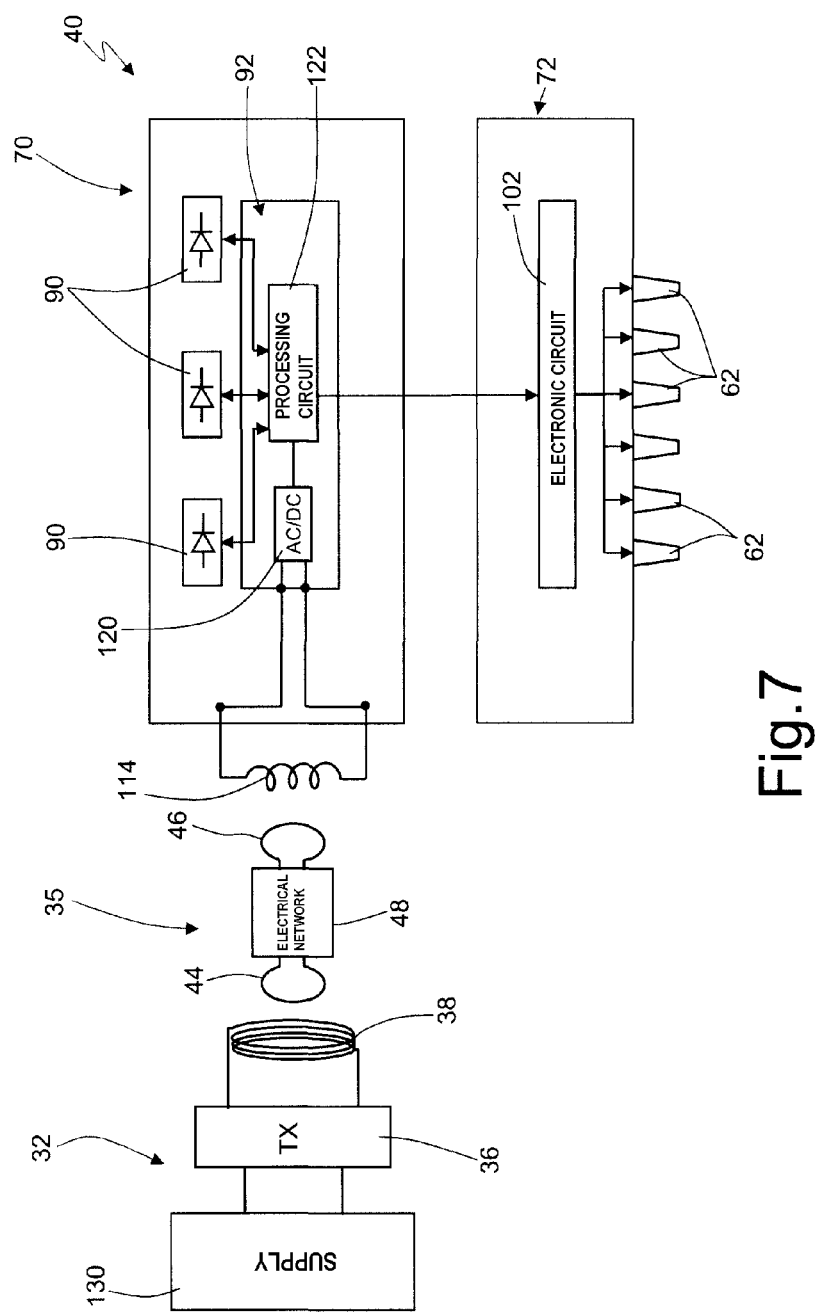
FIGS. 7, 10, 13 and 14 show block diagrams of different embodiments of the present retinal prosthesis.

In greater detail, inside the first body 74 a plurality of photodetectors 90 are present, which face the second surface 74b. In addition, inside the first body 74 a first electronic circuitry 92 is provided, which, as shown in FIG. 7, is electrically connected to the photodetectors 90, as described in detail hereinafter. Likewise present inside the first body 74 is a plurality of so-called through-silicon vias (TSVs) 94, which will be referred to hereinafter as "first vias 94".

In particular, the first vias 94 extend from the second surface 74b, up to the fourth surface 80a; hence, they traverse both the first body 74 and the first insulating region 80. In addition, the first vias 94 extend laterally with respect to the plurality of photodetectors 90. Again, even though this is not shown in FIG. 6, in a way in itself known the first electronic circuitry 92 is electrically connected to the first vias 94, through one or more of the first connection lines 78.

As regards the second chip 72, it extends underneath the fourth surface 80a, in direct contact with the first insulating region 80. Furthermore, the second chip 72 comprises a second body 98 of semiconductor material and a second connection region 100.

In greater detail, the second body 98 is delimited at the bottom by a sixth surface 98a, and is delimited at the top by a seventh surface 98b. The second connection region 100, instead, is arranged between the first insulating region 80 and the second body 98, with which it is in direct contact, and consequently is arranged between the fourth and seventh surfaces 80a, 98b.

In greater detail still, provided within the second body 98 is a second electronic circuitry 102. Moreover present within the second body 98 is a second plurality of through-silicon vias (TSVs) 104, which will be referred to hereinafter as "second vias 104". The second vias 104 extend from the seventh surface 98b and traverse the second body 98 entirely, protruding at least in part underneath the sixth surface 98a. In practice, the portions of second vias 104 that extend underneath the sixth surface 98a form the aforementioned electrodes 62.

As regards, instead, the second connection region 100, it may comprise one or more dielectric layers (not shown), as well as one or more metal connection lines 106, which will be referred to hereinafter as "second connection lines 106". In addition, the second connection region 100 houses a plurality of pads 108 of conductive material, which face the fourth surface 80a and each contact a respective first via 94.

Even though this is not shown in FIG. 6, in a way in itself known, the pads 108 are electrically connected to the second connection lines 106, to which also the second electronic circuitry 102 is electrically connected. Furthermore, in a way in itself known, the second electronic circuitry 102 is electrically connected to the second vias 104 through one or more of the second connection lines 106.

The stimulating unit 40 further comprises a dielectric region 110 and a local antenna 114. In particular, the dielectric region 110 extends above the first chip 70. In greater detail, the dielectric region 110 extends above the fifth surface 82a, in direct contact with the passivation region 82.

The local antenna 114 is a spiral antenna and is hence formed by a plurality of loops 116 of conductive material, arranged coplanar and concentric, within the dielectric region 110. In top plan view, the loops of the local antenna 114 may have, for example, a polygonal or circular shape.

In greater detail, the local antenna 114 has a first terminal 114a and a second terminal 114b, which are physically and electrically connected to a first conductive element 117a and a second conductive element 117b, which extend vertically starting from said first and second terminals 114a, 114b, and traverse, respectively, the aforementioned first and second windows 84, 86, as far as the third surface 76a, i.e., until they contact the first connection region 76.

In detail, even though this is not shown in FIG. 6, the first and second conductive elements 117a, 117b are in electrical contact with the first connection lines 78, and in particular with two distinct first connection lines, which are moreover in electrical contact with the first electronic circuitry 92. In practice, the first electronic circuitry 92 and the first and second terminals 114a, 114b are connected to the first connection lines 78 in such a way that, as shown in FIG. 7, the local antenna 114 is electrically connected to the first electronic circuitry 92.

In greater detail, the first electronic circuitry 92 comprises an AC/DC converter 120, and the local antenna 114 is electrically connected to the AC/DC converter 120.

Furthermore, as mentioned previously, the first electronic circuitry 92 and the photodetectors 90 are electrically connected to the first electrical connection lines 78 in such a way that the first electrical circuitry 92 is electrically connected to the photodetectors 90.

More in particular, as shown once again in FIG. 7, the first electronic circuitry 102 comprises a processing circuit 122, which is electrically connected to the photodetectors 90. In a way in itself known, the processing circuit 122 is likewise connected to the AC/DC converter 120.

In addition, the first and second electronic circuitries 92, 102, the first connection lines 78, the first vias 94, the pads 108 and the second connection lines 106 are physically connected in such a way that, as shown in FIG. 7, the first and second electronic circuitries 92, 102 are electrically connected to one another. More in particular, the second electronic circuitry 102 is electrically connected to the processing circuit 122, and possibly also to the AC/DC converter 120 (connection not shown).

In practice, the dielectric region 110 forms the first element of a stack of three contiguous elements, the second and third elements being formed, respectively, by the first and second chips 70, 72.

In use, the stimulating unit 40 is set in such a way that the electrodes 62 will contact the portion of retina to be stimulated, and hence with the dielectric region 110 facing the crystalline lens. Consequently, the light rays coming from the outside world, after traversing the crystalline lens, impinge on the dielectric region 110, which is transparent to visible light, i.e., does not absorb (to a first approximation) visible light.

In greater detail, in order to enable the light rays to impinge on the photodetectors 90, the local antenna 114, and in particular the loops 116, and the first connection lines 78 are arranged so as not to be superimposed on the photodetectors 90. In this way, the light rays can traverse the dielectric region 110, the passivation region 82 (which is also transparent to visible light), and the first connection region 76, the dielectric layers of which are also transparent to visible light, and finally impinge on the photodetectors 90.

Operatively, following upon reception of light rays, the photodetectors 90 generate corresponding electrical response signals, which are received by the processing circuit 122, which processes them in order to supply to the second electronic circuitry 102 corresponding electrical control signals. In turn, following upon reception of the electrical control signals, the second electronic circuitry 102 generates on the second vias 104, and hence on the electrodes 62, corresponding electrical stimulation signals, which electrically stimulate the portion of retina to be stimulated.

In order to enable the operation described, the stimulating unit 40 can be supplied through the electromagnetic expansion 35. In particular, as shown once again in FIG. 7, assuming that the transmitter 36 is connected to a supply 130 (for example, a battery) designed to supply electrical energy to the transmitter 36 itself, the transmitter 36 emits a supply signal, of a magnetic or electromagnetic type. This supply signal energizes the electromagnetic expansion 35, which resonates, reproducing the supply signal, i.e., emitting a replica (isofrequency signal) of the supply signal and focusing the corresponding electromagnetic field within the second portion of space $S_2$, delimited by the loop forming the second expansion antenna 46. Consequently, the replica of the supply signal is received by the local antenna 114, and hence also by the AC/DC converter 120, which generates a corresponding continuous-time signal, the power of which enables operation of the stimulating unit 40.

In particular, the power associated to the continuous-time signal enables operation of the processing circuit 122. Furthermore, it is possible for part of the power associated to the continuous-time signal to be supplied, in a way in itself known, to the second electronic circuitry 102, thanks to the fact that the first and second electronic circuitries 92, 102 are electrically connected to one another, or else by means of the connection between the AC/DC converter 120 and the second electronic circuitry 102, if this is present.

It should moreover be noted that, in a way in itself known, the first electronic circuitry 92, when supplied in the way described previously, is able to bias the photodetectors 90, enabling operation thereof.

It should likewise be noted that, in the absence of the electromagnetic expansion 35, the supply signal could not reach the local antenna 114, if not after undergoing a high attenuation within the vitreous body. In this case, the power associated with the continuous-time signal would be insufficient for operation of the stimulating unit 40.

In addition, it should be noted that, even though these are not shown, within the dielectric region 110 there may be arranged optical filters designed to filter one or more wavelengths. These filters may be set so as to be arranged on top of the photodetectors 90. Moreover, on the dielectric region 110, in direct contact therewith, it is possible for one or more lenses to be present, having the function of focusing the light rays on the photodetectors 90.

Figure 8:
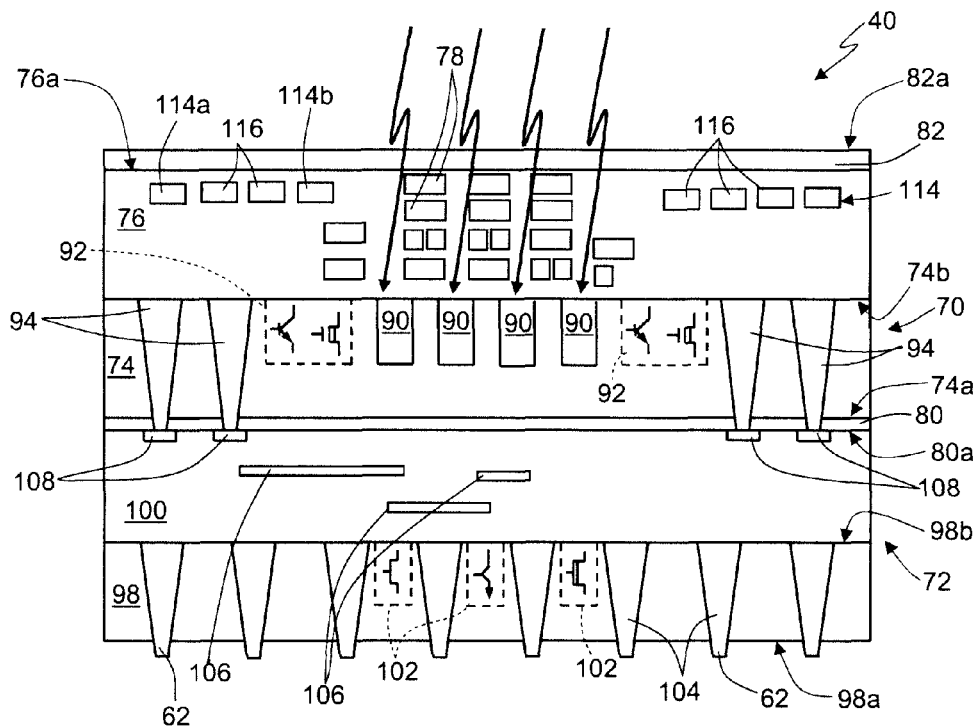

As shown in FIG. 8, it is likewise possible that the stimulating unit 40 is without the dielectric region 110, in which case the local antenna 114 extends inside the first connection region 76 so as to contact the first connection lines 78 without its own loops 116 being arranged on top of on the photodetectors 90. In this case, the local antenna 114 is hence formed in a monolithic way inside the first chip 70. Consequently, even though this is not shown in FIG. 8, the first and second terminals 114a and 114b are electrically connected to the first connection lines 78, without interposition of the first and second conductive elements 117a, 117b.

Figure 9:
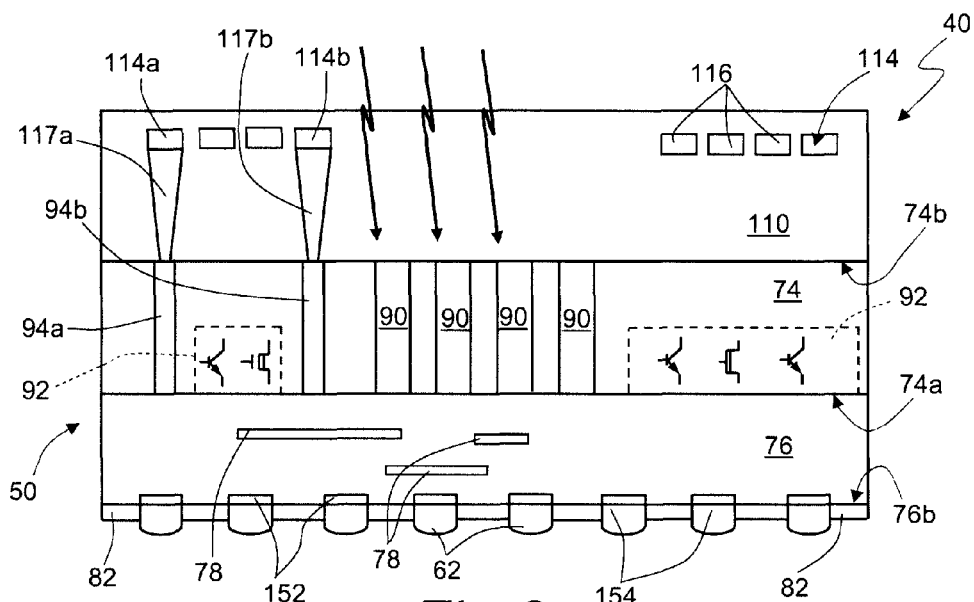

As shown in FIG. 9, the stimulating unit 40 may even be different. In particular, the stimulating unit 40 may not comprise the second chip 72. In this case, the first chip 70 is arranged in such a way that the dielectric region 110 is arranged on top of the first body 74, whilst the first connection region 76 is arranged underlying the first body 74, with which it is in direct contact.

In other words, if we again define as "first and second surfaces 74a, 74b" the surfaces that delimit, respectively, the first body 74 at the bottom and at the top, the dielectric region 110 extends in direct contact with the second surface 74b. Furthermore, if we define an eighth surface 76b, which delimits the first connection region 76 at the bottom, the passivation region 82 extends underneath the first connection region 76, in direct contact with the eighth surface 76b.

Inside the first body 74, at least two first vias are present, designated by 94a and 94b, respectively, which will be referred to hereinafter as "first-element via 94a" and "second-element via 94b".

In detail, the first-element via 94a and the second-element via 94b extend between the first surface 74a and the second surface 74b. In addition, the first-element via 94a is electrically connected to the first conductive element 117a, whilst the second-element via 94b is electrically connected to the second conductive element 117b.

As regards, instead, the photodetectors 90, they are again provided inside the first body 74 so as to be able to detect the light rays; hence, they face the second surface 74b.

In greater detail, even though this is not shown in FIG. 9, the first electronic circuitry 92 and the photodetectors 90 are electrically connected to the first electrical connection lines 78 in such a way that the first electrical circuitry 92 is electrically connected to the photodetectors 90. Furthermore, the first electronic circuitry 92, the first-element via 94a and the second-element via 94b are electrically connected to the first electrical connection lines 78 in such a way that the first electrical circuitry 92 is electrically connected to the first and second terminals 114a, 114b of the local antenna 114.

In this embodiment, inside the first connection region 76 a plurality of pads is present, designated by 152, which face the eighth surface 76b and, even though this is not shown in FIG. 9, are electrically connected to the first connection lines 78. Furthermore, underneath, and in electrical contact with, each of said pads 152, a corresponding bump 154 of conductive material is present.

In detail, the bumps 154 extend through the passivation region 82, protruding at least in part underneath the passivation region 82 itself. In this way, the portions of bumps 154 that extend beyond the passivation region 82 function as electrodes 62.

Figure 10:
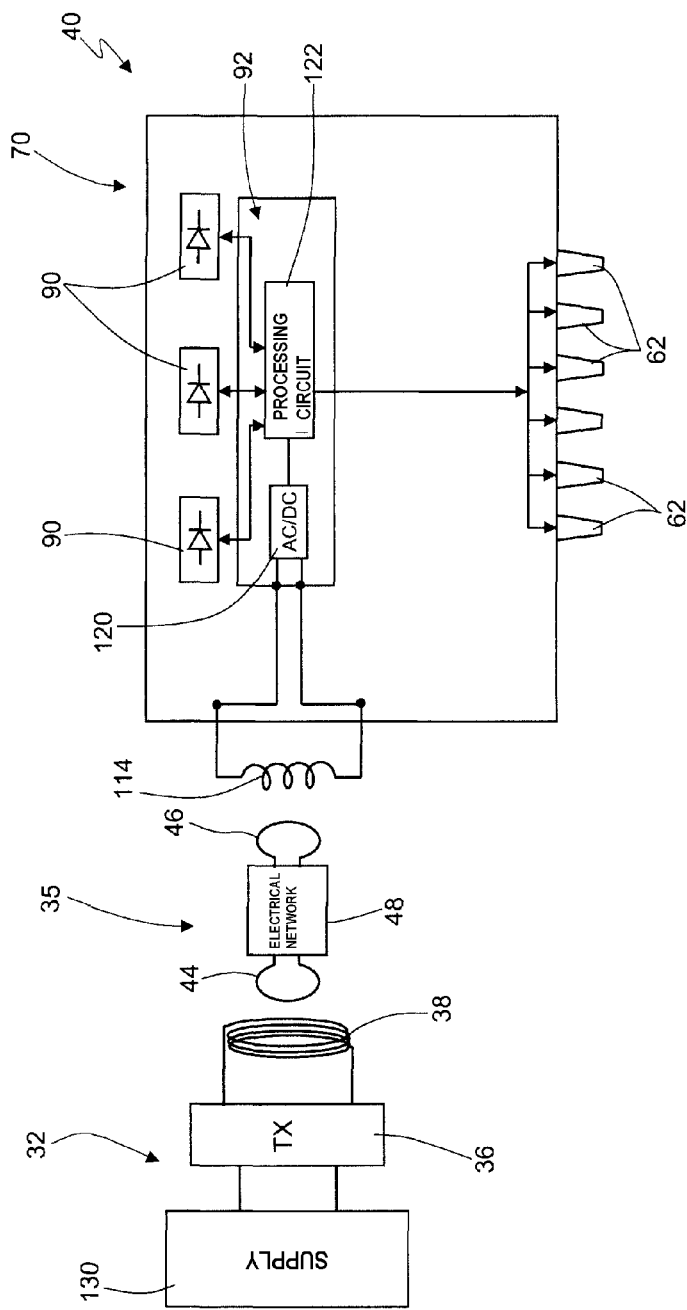

In greater detail, the pads 152 and the first electronic circuitry 92 are electrically connected to the first connection lines 78 in such a way that the first electronic circuitry 92 is electrically connected to the pads 152 themselves, and hence also to the bumps 154. Consequently, the first electronic circuitry 92 can itself generate, for example by means of the processing circuit 122, the electrical stimulation signals to be supplied to the electrodes, without the need to use the second chip 72, as shown in FIG. 10.

Figure 11:
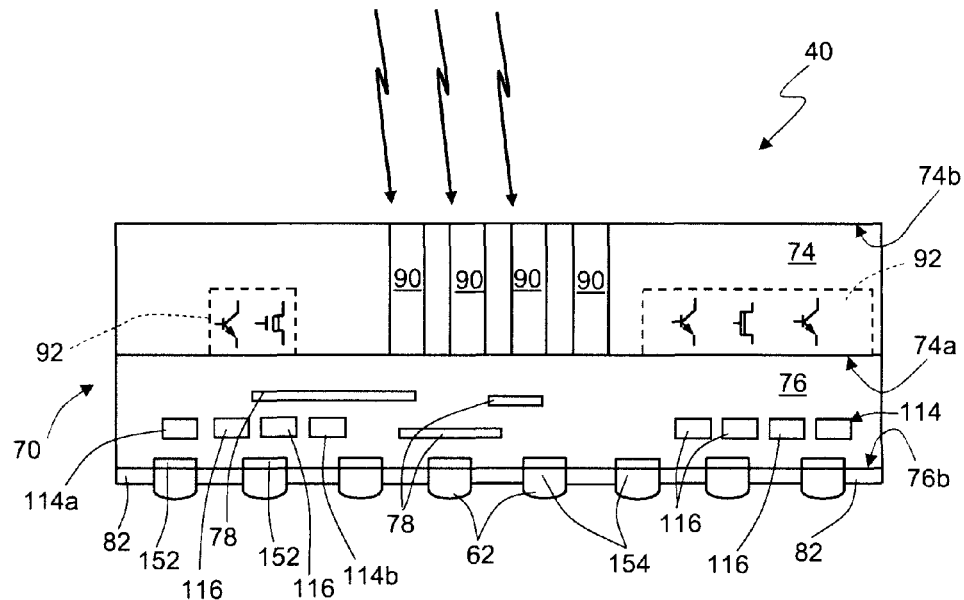

As shown in FIG. 11, according to a further embodiment, the stimulating unit 40, in addition to not including the second chip 72, is without the dielectric region 110. Again, according to said embodiment, the first chip 70 may not comprise any first via inside the first body 74.

In detail, with respect to what is shown in FIG. 9, the local antenna 114 is formed in a monolithic way inside the first chip 70 and extends inside the first connection region 76 so as to contact the first connection lines 78. In practice, even though this is not shown in FIG. 11, the first and second terminals 114a and 114b of the local antenna 114 are electrically connected to the first connection lines 78, without interposition of the first and second conductive elements 117a, 117b, and in such a way that these first and second terminals 114a, 114b are electrically connected to the first electronic circuitry 92.

Figure 12:
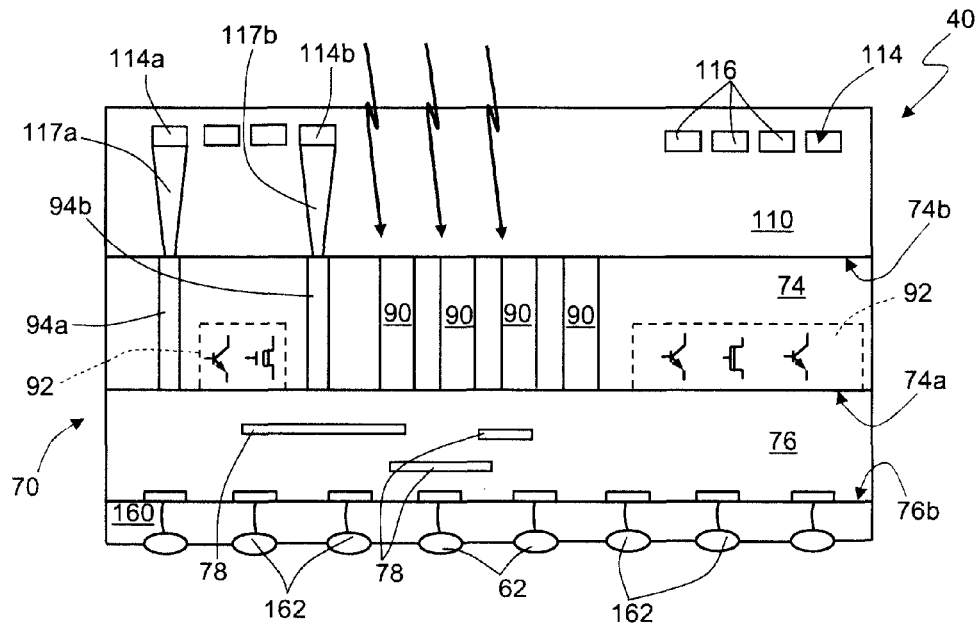

As shown by way of example in FIG. 12, likewise possible is an embodiment in which the stimulating unit 40 is similar to the one shown in FIG. 9, but is without the passivation region 82 and the bumps 154. Furthermore, the stimulating unit 40 comprises an insulating layer 160 of elastic material, such as for example a polymeric material, arranged underneath the first connection region 76, in direct contact with the eighth surface 76b. In addition, the stimulating unit 40 comprises a plurality of probes 162 of conductive material, embedded within the insulating layer 160 so as to project at least in part underneath the insulating layer 160 itself. These probes 162 are electrically connected to the pads 152, and hence also to the first connection lines 78. In particular, the probes 162 are connected to the first connection lines 78 so that they are electrically connected to the first electronic circuitry 92. In practice, the portions of probes 162 that extend underneath the insulating layer 160 function as electrodes 62.

The embodiment shown in FIG. 12 hence reduces the mechanical stress undergone by the retina on account of the presence of the stimulating unit 40; in fact, the insulating layer 160 can adapt at least in part to the curvature of the retina.

In any case possible are hybrid embodiments, in which the stimulating unit 40 is formed by components described previously with reference to two or more of the above embodiments.

Figure 13:
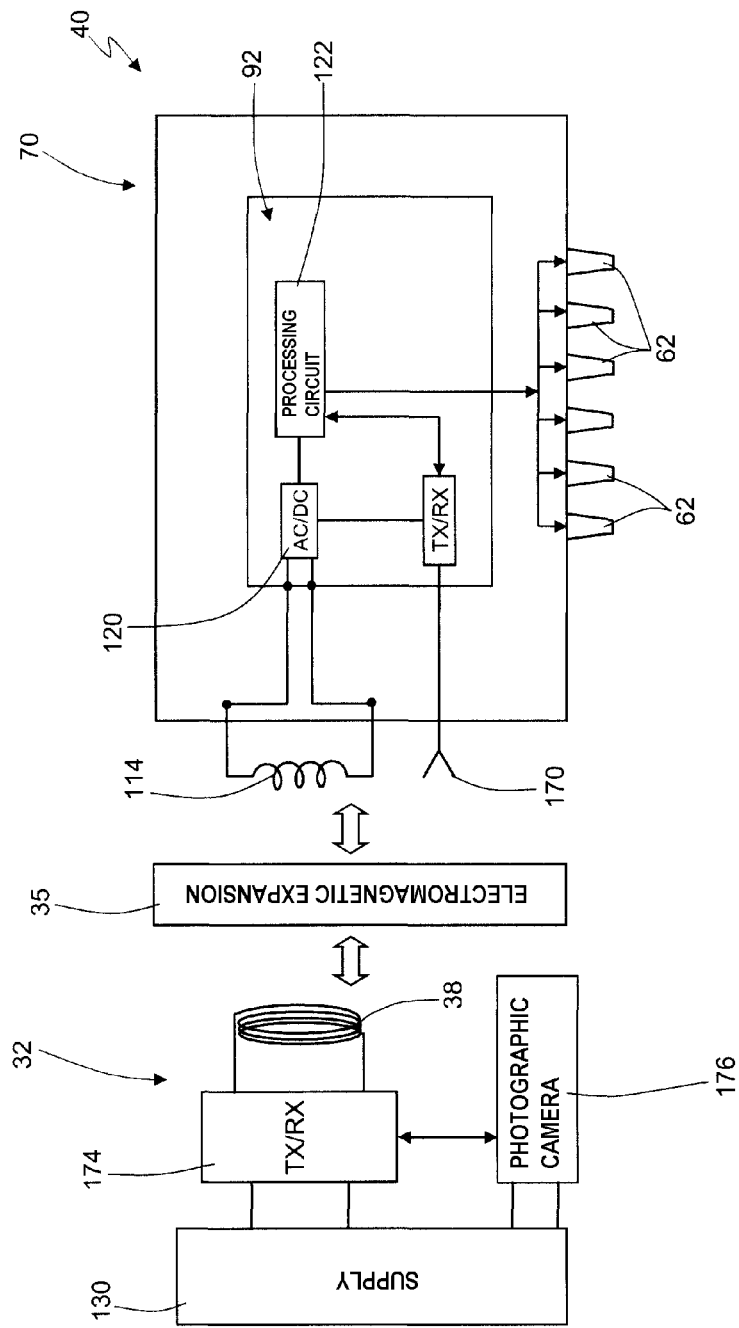

Furthermore, as shown in FIG. 13, it is possible for the stimulating unit 40 not to include any photodetector. In this case, the stimulating unit 40 includes an additional antenna 170 and an internal transceiver 172, which is for example formed inside the first electronic circuitry 92 and is electrically connected to the additional antenna 170 and to the AC/DC converter 120. Furthermore, in a way similar to what is shown in FIG. 10, the stimulating unit 40 may be without the second chip 72, even though embodiments (not shown) are in any case possible in which the stimulating unit 40 comprises the second chip 72, and which are in any case provided with the additional antenna 170 and the internal transceiver 172.

In the case of the embodiment illustrated in FIG. 13, the external unit 32 comprises, in addition to the supply 130 and to the external antenna 38, an external transceiver 174 and an image-acquisition device 176, such as, for example, a photographic camera, which are connected to one another and to the supply 130. The external antenna 38 is connected to the external transceiver 174.

Operatively, the image-acquisition device 176 can acquire images of the outside world, and send corresponding (electrical) image signals to the external transceiver 174, which sends them to the additional antenna 170, through the external antenna 38 and by interposition of the electromagnetic expansion 35. The local transceiver 172, supplied by the AC/DC converter 120, receives the image signals from the additional antenna 170, and supplies them to the processing circuit 122, which generates corresponding electrical stimulation signals.

The processing circuit 122 can moreover send feedback signals to the internal transceiver 172, which in turn sends them to the additional antenna 170, which irradiates them in such a way that, by interposition of the electromagnetic expansion 35, the feedback signals can be received by the external antenna 38, and then by the external transceiver 174.

The feedback signals may contain, for example, information on operation of the stimulating unit 40, which is hence made available to the external transceiver 174, for example for enabling a diagnostics of the stimulating unit 40 itself.

Figure 14:
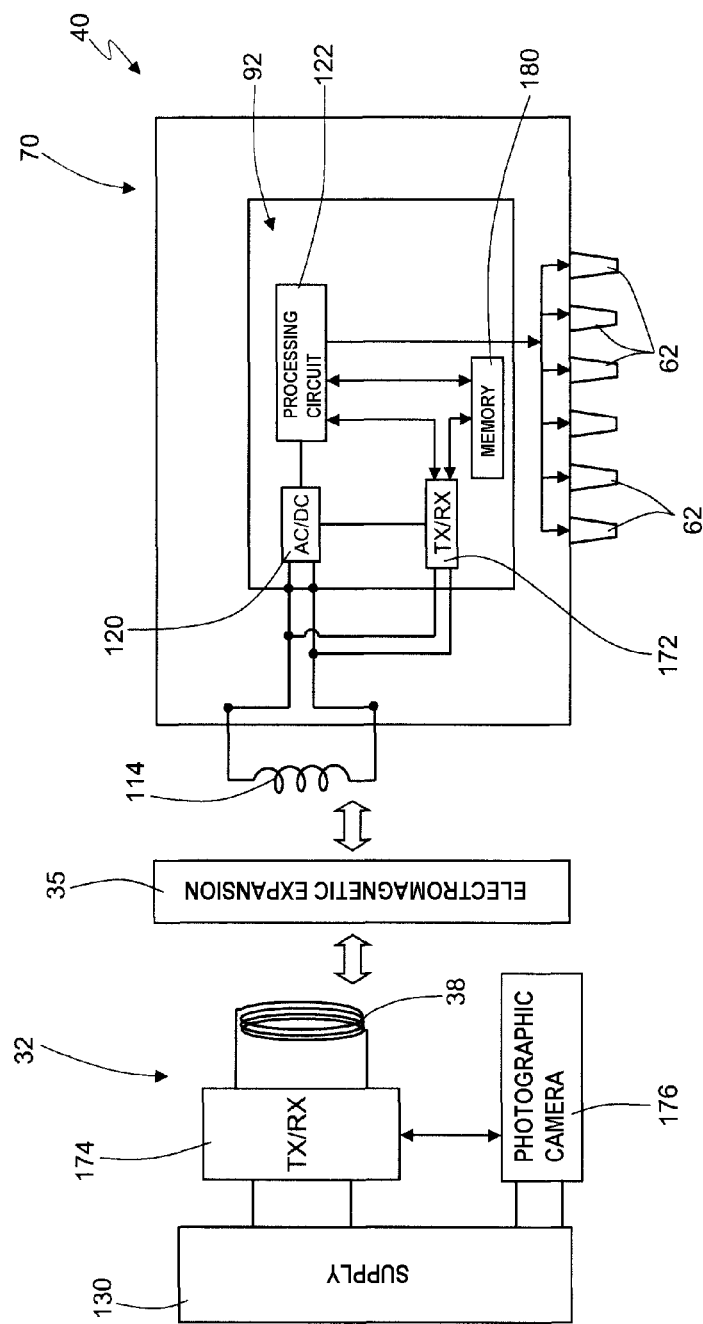

As shown in FIG. 14, it is likewise possible for the local antenna 114 to function also as additional antenna. In this case, the local transceiver 172 is connected not only to the AC/DC converter 120, but also to the local antenna 114 in such a way that both the image signals and the feedback signals are received/transmitted through the local antenna 114.

Furthermore, as shown by way of non-limiting example once again in FIG. 14, the processing circuit 122 may be of a programmable type. For this purpose, the first electronic circuitry 92 may comprise a memory 180, for example of a non-volatile type, connected both to the processing circuit 122 and to the internal transceiver 172.

According to this embodiment, the memory 180 may contain instructions, and the processing circuit 122 may be designed to read the instructions present in the memory 180 and program itself accordingly. More in particular, the instructions may be generated in a way in itself known by the external transceiver 174, which may generate corresponding programming signals, which are transmitted through the external antenna 38. Once the programming signals have been received, the internal transceiver 172 may load the corresponding instructions into the memory 180, in such a way that the processing circuit 122 programs itself accordingly.

Even though the embodiments described so far are of an epiretinal type, likewise possible are embodiments in which the retinal prosthesis 30 functions as prosthesis of a subretinal type. In this case, the stimulating unit 40 is arranged between the internal retina and the external retina, and oriented in such a way that the electrodes 62, whether they be formed by vias, bumps, or probes, contact the internal retina, and hence face the inside of the eye.

Figure 15:
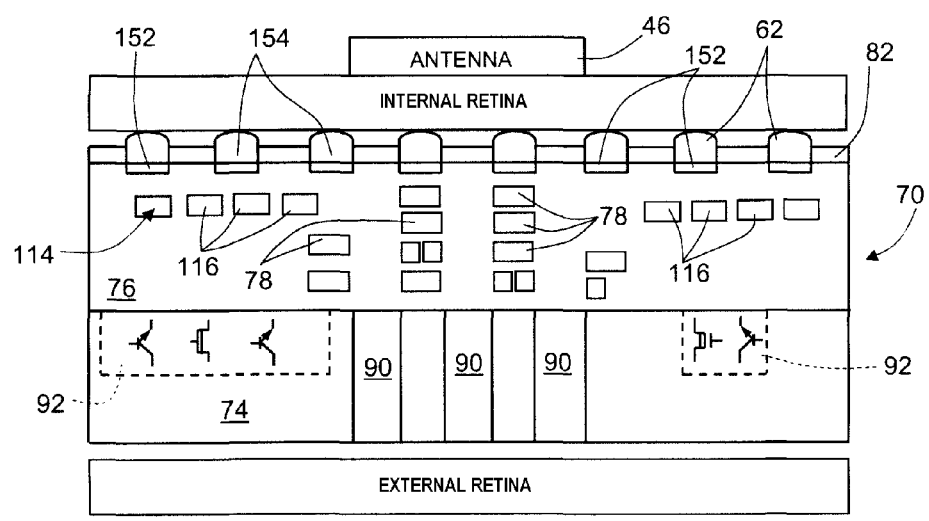

Purely by way of example, FIG. 15 shows an embodiment of prosthesis of a subretinal type, in which the stimulating unit 40 is of the type shown in FIG. 11, and is arranged in such a way that the bumps 154 contact the internal retina. With respect to the embodiment shown in FIG. 11, the first connection lines 78, the pads 152, and the bumps 154 are arranged so as not to overly the photodetectors 90 or the local antenna 114. In this embodiment, the second expansion antenna 46 is preferably arranged in contact with a portion of internal retina overlying the stimulating unit 40.

Figure 16:
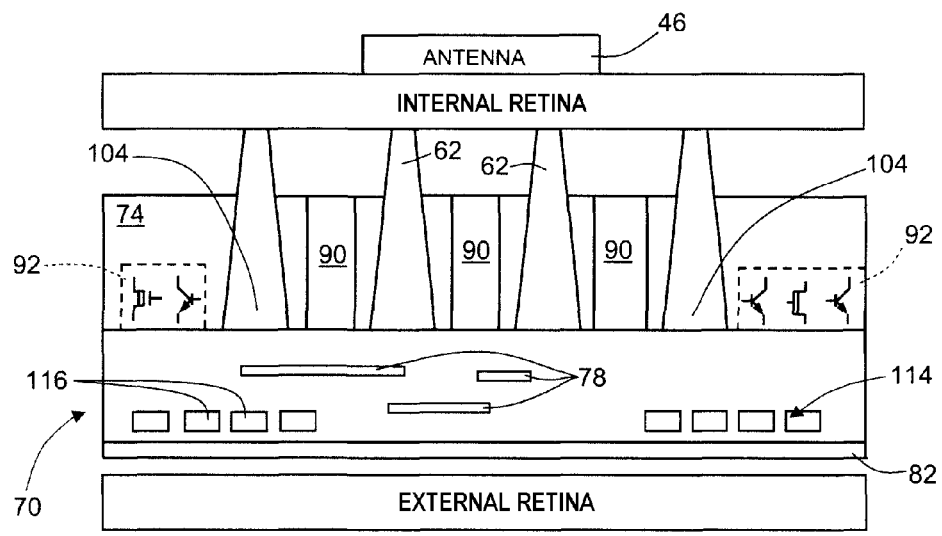

As shown in FIG. 16, it is likewise possible for the passivation region 82 of the first chip 70 to face the external retina in such a way that the first body 74 and the second vias 104 face the internal retina, the first connection region 76 being hence arranged between the first body 74 and the passivation region 82. The local antenna 114 is arranged inside the first connection region 76 and is connected to the first electronic circuitry 92, formed in the first body 74, by means of the first connection lines 78.

Moreover possible are further embodiments (not shown), both of an epiretinal type and of a subretinal type, in which the first expansion antenna 44 is arranged, in use, not in the proximity of the crystalline lens, but rather in the proximity of the inner wall of the bulb of the eye.

Figure 17:
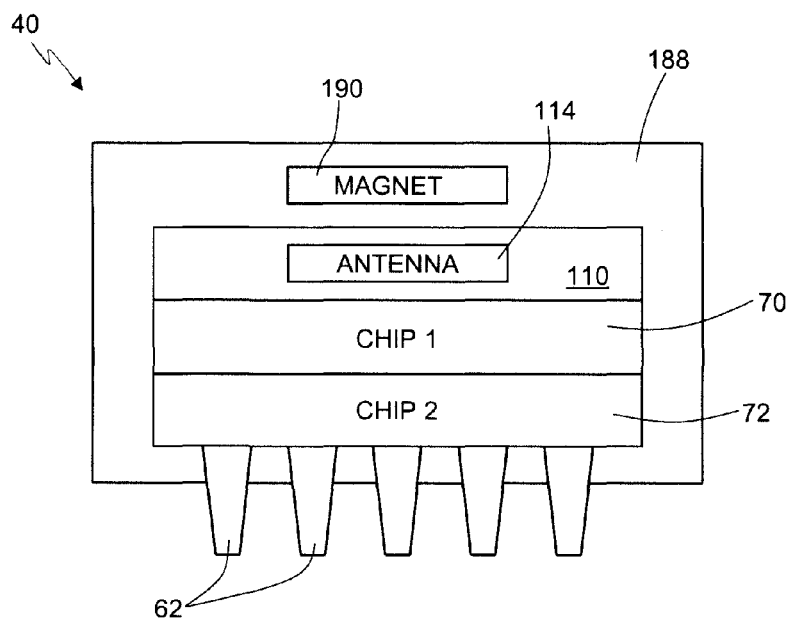

In addition, as shown purely by way of example in FIG. 17, specifically referring, without any loss of generality, to what is shown in FIG. 6, the stimulating unit 40 may comprise a hermetic package 188. This hermetic package 188 contains the first and second chips 70, 72, as well as the dielectric region 110, hence also the local antenna 114, with the sole exception of the portions of second vias 104 forming the electrodes 62.

In this way, the stimulating unit 40 is protected from the action of the biological liquids present inside the human eye, which have potentially corrosive effects on the components contained inside the hermetic package 188. Furthermore, the hermetic package 188 has the function of preventing any possible undesirable short-circuits, which can be set up on account of the fact that the vitreous body is a potentially conductive aqueous solution.

As shown for simplicity once again in FIG. 17, likewise possible are embodiments in which the stimulating unit 40 comprises a permanent magnet 190, the presence of which is consequently not necessarily associated with the presence of the hermetic package 188.

In detail, the permanent magnet 190 performs the function of constraining the stimulating unit 40 to the electromagnetic expansion 35, and in particular to the second expansion antenna 46, enabling preservation of the mutual positioning thereof. Other constraint devices (not shown) are in any case possible, such as for example mechanical hooks.

As regards, instead, the electromagnetic expansion 35, as mentioned previously, it is substantially flexible; hence, it can be bent in such a way that the first and second expansion antennas 44, 46, as well as, possibly the electrical network 48 (in particular, in the case where it is formed by two wires of conductive material coated of the protective coating 50) are set coplanar.

Figure 18A:
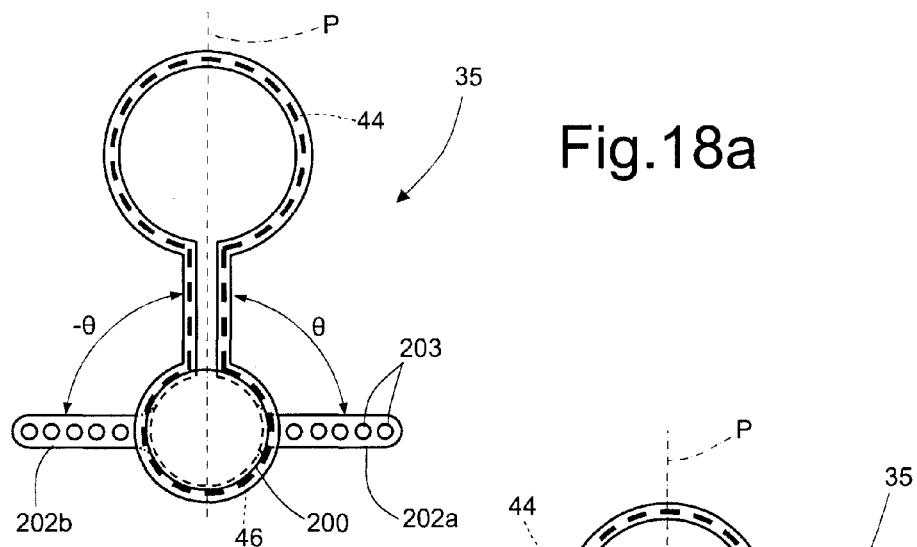
FIGS. 18a, 18b are schematic illustrations of front views of one and the same electromagnetic expansion, in two different operating conditions.

Furthermore, the electromagnetic expansion 35 can comprise a first supporting element 200 and at least one arm, as shown by way of example in FIG. 18a, where a first arm 202a and a second arm 202b are shown. In particular, the first and second arms 202a, 202b are made of an insulating and elastic material, such as for example parylene, and may each present a plurality of holes 203, designed to enable the passage of possible biological liquids through the first and second arms 202a, 202b themselves.

In detail, the first supporting element 200 is arranged coaxial with respect to the loop of the second expansion antenna 46, and is fixed with respect to the second expansion antenna 46 itself. Furthermore, the first and second arms 202a, 202b are hinged with respect to the first supporting element 200; hence, they are hinged with respect to the second expansion antenna 46, with respect to which they can rotate through 360° about a first axis of rotation $A_1$ coinciding with the axis of the loop of the second expansion antenna 46. In addition, the first and second arms 202a, 202b can rotate about the first axis of rotation $A_1$ independently of one another.

In greater detail, in what follows it will be assumed, for simplicity of description, that the electrical network 48 is formed by two wires of conductive material, and defined as "resting state" is the situation in which the electromagnetic expansion 35 is arranged coplanar, with the wires of conductive material straight and with the first and the second arms 202a, 202b straight. Moreover defined as "main axis P" is the axis that, when the electromagnetic expansion 35 is in the resting state, joins the centers of the loops of the first and second expansion antennas 44, 46. In the resting state, the axis P is perpendicular to the first axis of rotation $A_1$.

Given this, with reference, for simplicity of description, to the resting state, the electromagnetic expansion 35 can assume a first operative condition and a second operative condition, different from one another.

Figure 18B:
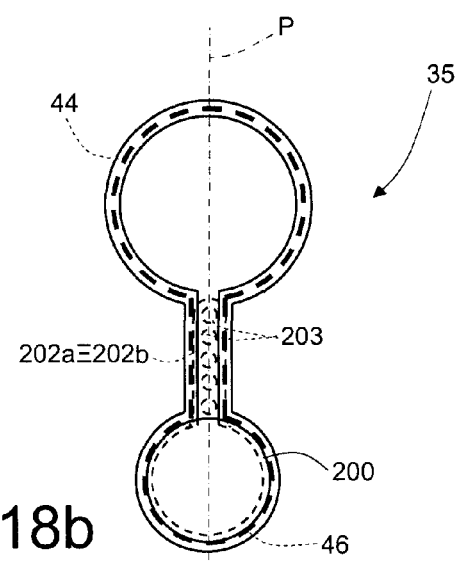
Figure 18C:
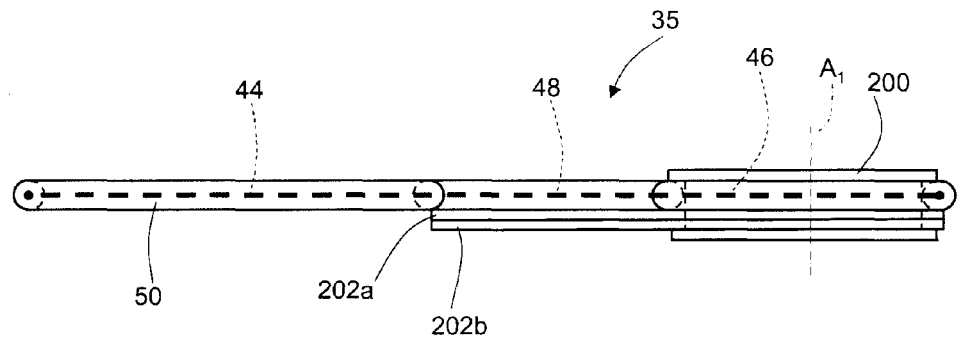
FIG. 18c is a schematic illustration of a side view of the electromagnetic expansion shown in FIGS. 18a and 18b.
Figure 19:
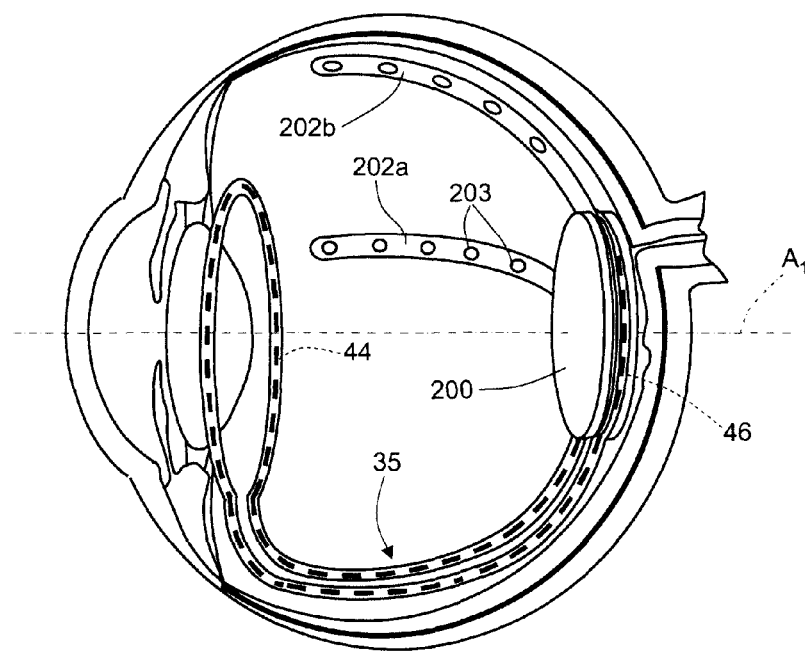
FIG. 19 is a schematic illustration of an internal view of a bulb of the eye housing the electromagnetic expansion shown in FIGS. 18a-18c.

In detail, as shown in FIGS. 18b and 18c, in the first operative condition the first and second arms 202a, 202b are aligned along the main axis P, and form zero angles with this main axis P so as to reduce the overall dimensions of the electromagnetic expansion 35. In other words, the first and second arms 202a, 202 are arranged on top of on one another.

Instead, in the second operative condition, illustrated in FIG. 18a, the first and second arms 202a, 202b are able to rotate with respect to the main axis P through one and the same angle θ, one in a clockwise direction, and the other in the counterclockwise direction. For example, the angle θ may be of 90°. It is in any case possible to rotate the first and second arms 202a, 202b through a different angle θ, or also through respective different angles.

Consequently, it is possible to implant in the eye the electromagnetic expansion 35 in the resting state and in the first operative condition, i.e., when the electromagnetic expansion 35 presents least encumbrance, and then rotate the first and second arms 202a, 202b in such a way that the electromagnetic expansion 35 assumes the second operative condition.

In greater detail, as mentioned previously, it is possible to bend the electromagnetic expansion 35 in an operative state, which differs from the resting state and in which the first axis of rotation $A_1$ coincides with the axes of the loops of the first and second expansion antennas 44, 46. In said operative state, once the first and second arms 202a, 202b are rotated in the second operative condition, they can contact the inner wall of the bulb of the eye (and hence, the retina itself), and exert a pressure on this inner wall, enabling the electromagnetic expansion 35 to remain constrained to the inner wall of the bulb of the eye, without any need for sutures. For this purpose, the first and second arms 202a, 202b may present a marked roughness to increase the friction with the inner wall of the bulb of the eye.

In greater detail, assuming once again, without this implying any loss of generality, that the electrical network 48 is formed by two wires of conductive material (coated by the protective coating 50), the loops of the first and second expansion antennas 44, 46, the wires of conductive material, the protective coating 50, and the first and second arms 202a, 202b are made of materials and have dimensions such that at least a portion of the wires of the electrical network 48 and the first and second arms 202a, 202b can be bent, once inserted in the eye and starting from the resting state, so as to assume at least locally, and to a first approximation, the curvature of the inner wall of the bulb of the eye (on the simplifying hypothesis that the inner wall of the bulb of the eye has in every point one and the same curvature).

Figure 20:
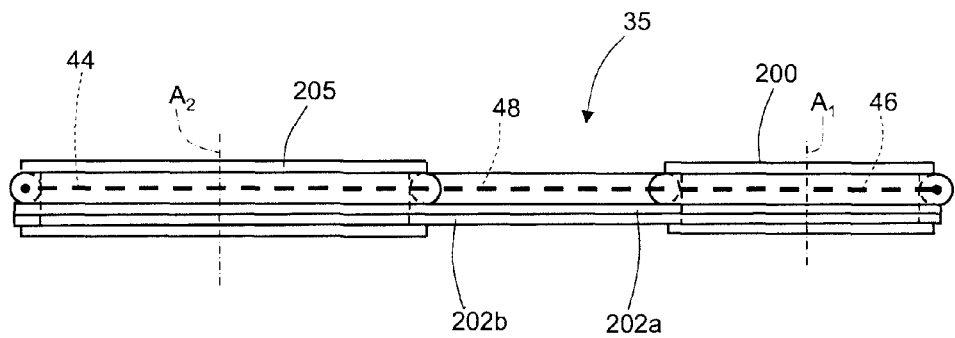
FIG. 20 is a schematic illustration of a side view of a variant of the electromagnetic expansion shown in FIGS. 18a-18c.

As shown in FIG. 20, the electromagnetic expansion 35 may likewise comprise a second supporting element 205, arranged coaxial with respect to the loop of the first expansion antenna 44 and fixed with respect to the first expansion antenna 44 itself. In this case, the first and second arms 202a, 202b are hinged also to the second supporting element 205, and are hence hinged also to the first expansion antenna 44, with respect to which they can (in given conditions described hereinafter) rotate, independently of one another, through 360° about a second axis of rotation $A_2$ coinciding with the axis of the loop of the first expansion antenna 44. In the resting state, the second axis of rotation $A_2$ is parallel to, and distinct from, the first axis of rotation $A_1$. Consequently, in the resting state, the first and second arms 202a, 202b cannot rotate.

Figure 21:
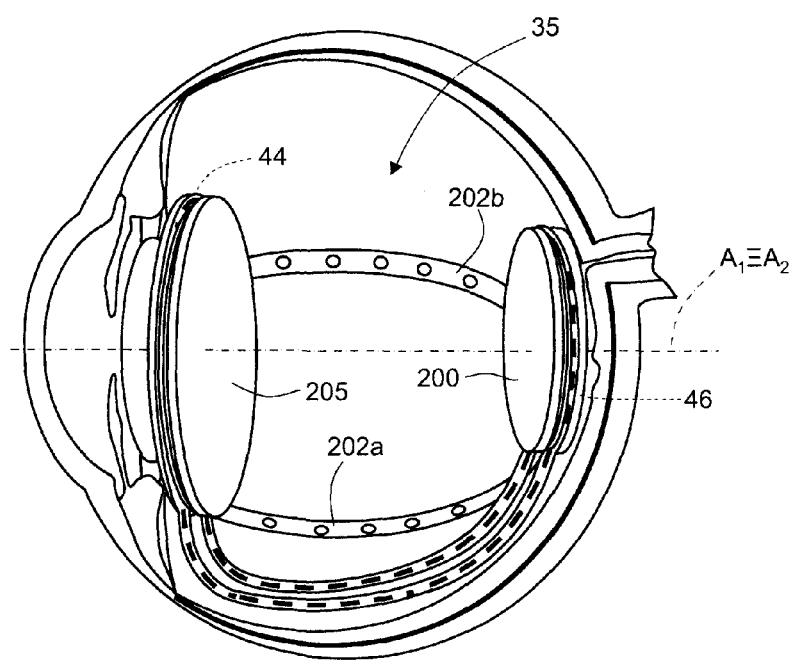
FIG. 21 is a schematic illustration of an internal view of a bulb of the eye housing the electromagnetic expansion shown in FIG. 20.

As shown in FIG. 21, after insertion of the electromagnetic expansion 35 into the eye, it is possible to bend the electromagnetic expansion 35 in such a way that the first and second axes of rotation $A_1$ and $A_2$ coincide (operative state). In this way, the first and second arms 202a, 202b can in any case rotate with respect to the (coinciding) axes of the loops of the first and second expansion antennas 44, 46, thus enabling the second operative condition to be set.

Figure 22:
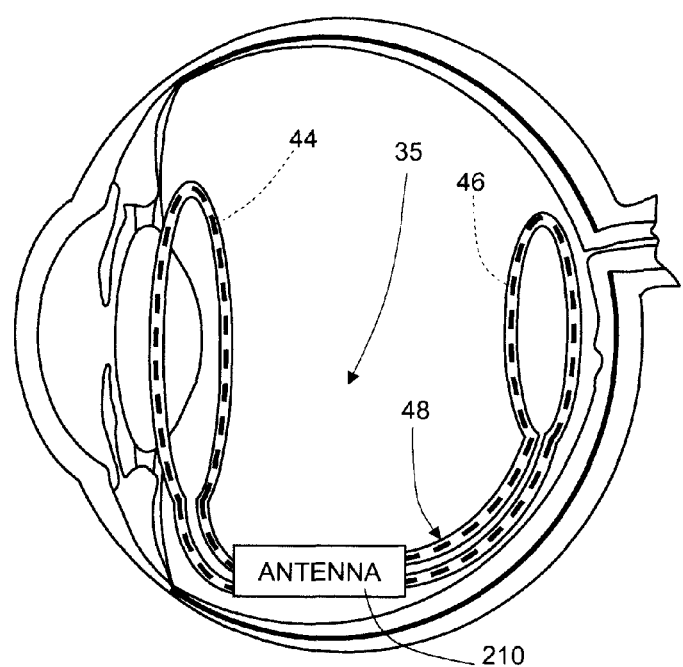
FIG. 22 is a schematic illustration of an internal view of a bulb of the eye housing a variant of the electromagnetic expansion.

It should moreover be noted that the electromagnetic expansion 35 may comprise a third expansion antenna 210, which, as shown in FIG. 22, may be arranged between the first and second expansion antennas 44, 46, to which it is electrically connected. In practice, the electrical network 48 comprises, amongst other things, the third expansion antenna 210.

Figure 23:
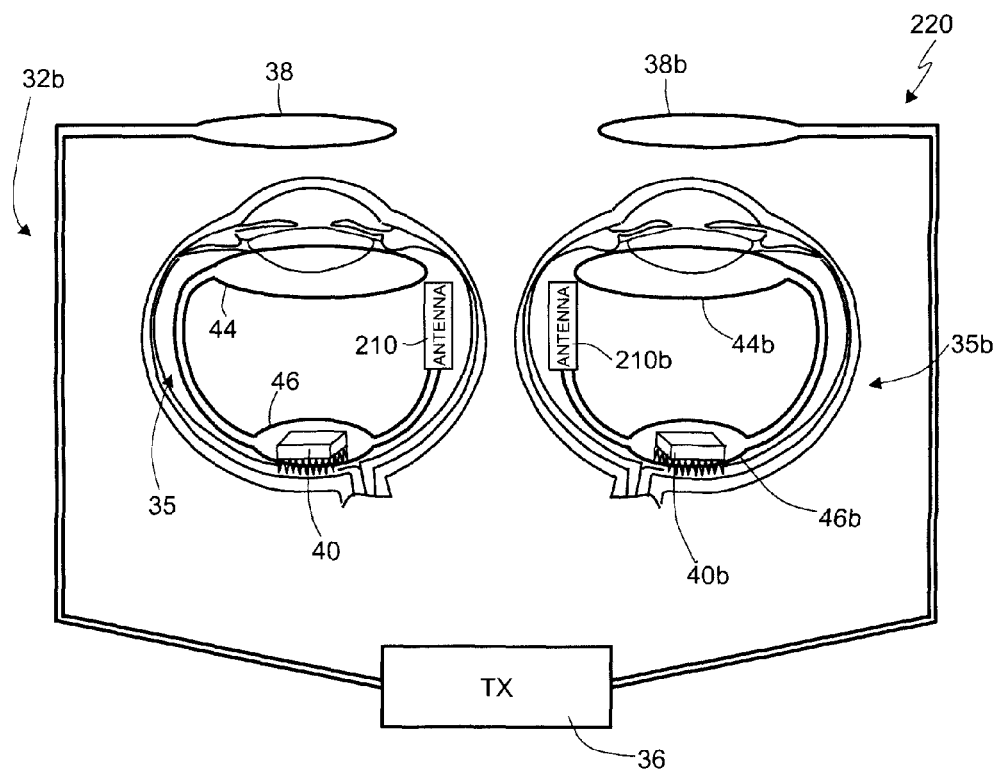
FIG. 23 is a schematic illustration of a block diagram of an electronic system for visual aid.

Consequently, the third expansion antenna 210 may even be connected just to the second expansion antenna 46, which is hence arranged between the first and third expansion antennas 44, 210, as shown in FIG. 23, which represents an electronic system for visual aid 220.

In detail, the electronic system for visual aid 220 comprises, in addition to the electromagnetic expansion 35 and to the stimulating unit 40, an additional electromagnetic expansion 35b and an additional stimulating unit 40b. The first, second, and third expansion antennas of the additional electromagnetic expansion 35b are respectively designated by 44b, 46b and 210b, and are connected in a way similar to the case of the electromagnetic expansion 35, i.e., in such a way that the second expansion antenna 46b is arranged between the first and third expansion antennas 44b, 210b.

In detail, assuming that the stimulating unit 40 and the electromagnetic expansion 35 are implanted in a first eye of a patient, the additional stimulating unit 40b and the additional electromagnetic expansion 35b are implanted in the second eye of the patient.

Furthermore, the electromagnetic expansion 35 and the additional electromagnetic expansion 35b are arranged in such a way that the respective third expansion antennas 210 and 210b are as close as possible. The external unit, here designated by 32b, may then comprise an additional external antenna 38b, which is to be set in the proximity of the second eye of the patient, and is also connected to the transmitter 36.

In use, the electronic system for visual aid 220 enables, amongst other things, exchange of data between the stimulating unit 40 and the additional stimulating unit 40b; for this purpose, they each comprise internal transceivers, even though they are not shown in FIG. 23.

Figure 24:
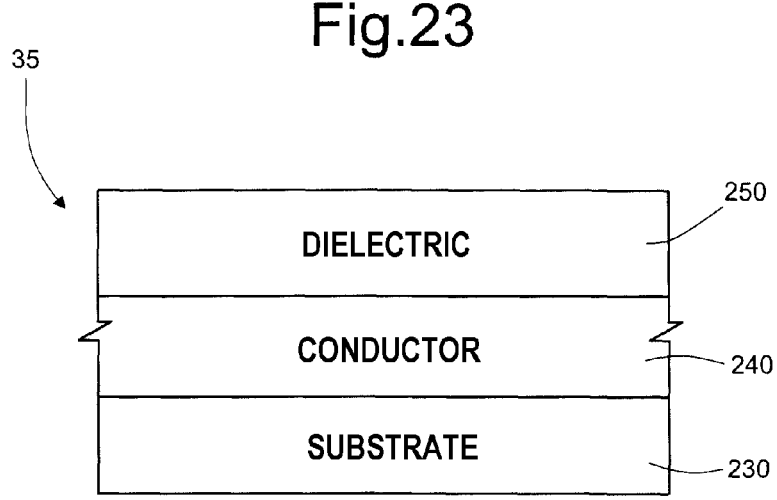
FIG. 24 is a schematic illustration of a cross section of a portion of electromagnetic expansion.

Finally, it should be noted that in general, instead of the protective coating 50, the electromagnetic expansion 35 may comprise a substrate 230 of dielectric material, a conductive layer 240, overlying the substrate 230, and a top layer 250 of dielectric material. Even though they are not shown in detail in FIG. 24, the first and second expansion antennas 44, 46, as well as the electrical network 48 may be formed in the conductive layer 240.

The advantages that the present retinal prosthesis afford emerge clearly from the foregoing discussion. In particular, in the case where the stimulating unit 40 gets damaged, it is not necessary to remove, from the eye, also the electromagnetic expansion 35, which represents the bulkiest portion of the internal unit 34. In addition, since the electromagnetic expansion 35 is not in ohmic contact with the stimulating unit 40, it is technologically simpler to produce the hermetic package 188, from which the electrodes usually exit. In this way, there is an optimized prevention of possible accidental short-circuits in the stimulating unit 40 itself due to the presence of potentially conductive biological liquids.

Finally, it is evident that modifications and variations may be made to the retinal prosthesis described, without thereby departing from the scope of the present invention.

For example, the electromagnetic expansion 35 may present devices for fixing to the internal walls of the bulb of the eye that are additional or alternative to the first and second arms 202a, 202b. Furthermore, the number and shape of the arms described are not limiting.

In addition, the first, second, and third (if present) expansion antennas 44, 46, 210 may be of a type different from the one described; for example, one or more of them may be helical antennas.

Likewise, also the local antenna 114 may differ from the one shown; for example, it may also be a helical antenna.

As regards the arrangement of the stimulating unit 40 with respect to the electromagnetic expansion 35, it may differ with respect to the one shown or described.

For example, also in the case of a prosthesis of an epiretinal type, the stimulating unit 40 may be arranged outside the portion of space $S_2$.

As regards, instead, the first and second axes of rotation $A_1$, $A_2$, they may not coincide with the axes of the loops of the first and second expansion antennas 44, 46.

Finally, it is possible to implant within one and the same eye a number of electromagnetic expansions, it being possible for each of them to be optimized so as to function, for example, in a respective frequency band. For example, within one and the same eye a main electromagnetic expansion and a secondary electromagnetic expansion may be present, which may be physically independent, or else may share one and the same antenna. In addition, the expansion antennas and the electrical network of the main electromagnetic expansion may be provided on a first face of a generic substrate, whilst the expansion antennas and the electrical network of the secondary electromagnetic expansion may be provided on a second face of the generic substrate.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A retinal prosthesis comprising:
an electronic stimulation unit, which is configured to be housed inside an eye, the electronic stimulation unit comprising:
a plurality of electrodes, configured to contact a portion of a retina of the eye;
an electronic control circuit electrically connected to said electrodes and configured to supply to the electrodes electrical stimulation signals designed to stimulate said portion of retina; and
a local antenna packaged in the electronic stimulation unit and connected to the electronic control circuit; and
an electromagnetic expansion, which is configured to be housed inside the eye, the electromagnetic expansion comprising:
a first expansion antenna; and
a second expansion antenna electrically coupled with the first expansion antenna, wherein the first expansion antenna is coupleable magnetically or electromagnetically to an external antenna, and the second expansion antenna is coupleable magnetically or electromagnetically to said local antenna, and
wherein the electromagnetic expansion is further configured to receive an electromagnetic supply signal transmitted by said external antenna and generate a corresponding replica signal for reception in the local antenna.

2. The retinal prosthesis according to claim 1, wherein the electronic control circuit comprises a supply stage connected to the local antenna and configured to generate, following upon reception of the replica signal, a converted signal to supply the electronic control circuit.

3. The retinal prosthesis according to claim 2, wherein said supply stage comprises an AC/DC converter.

4. The retinal prosthesis according to claim 1, wherein the electromagnetic expansion is configured to resonate in response to reception of the electromagnetic supply signal.

5. The retinal prosthesis according to claim 1, wherein the electromagnetic expansion further comprises an electrical network including at least one of a reactive element and a matching network configured to match the impedances of the first and second expansion antennas.

6. The retinal prosthesis according to claim 1, wherein the electromagnetic expansion comprises at least one arm hinged to the second expansion antenna about a first axis of rotation.

7. The retinal prosthesis according to claim 6, wherein the electromagnetic expansion is elastically displaceable between a resting state, where the arm is straight, and an operative state, where the arm substantially assumes, at least locally, a radius of curvature of an inner wall of the eye.

8. The retinal prosthesis according to claim 6, wherein the arm is hinged to the first expansion antenna about a second axis of rotation, and the electromagnetic expansion is elastically displaceable between a resting state, in which the first and second axes of rotation are distinct, and an operative state, in which the first and second axes of rotation coincide.

9. The retinal prosthesis according to claim 1, wherein the electronic stimulation unit comprises a dielectric region, a first connection region housing first conductive connection lines, and a first body of semiconductor material, the first body being arranged between, and in direct contact with, the dielectric region and the first connection region, the electronic control circuit being formed at least in part inside the first body; and wherein the local antenna is housed inside the dielectric region and is connected to the electronic control circuit by the first conductive connection lines and by a pair of conductive elements that extend through the first body.

10. The retinal prosthesis according to claim 1, wherein the electronic stimulation unit comprises a first connection region housing first conductive connection lines, and a first body of semiconductor material contiguous to the first connection region, the electronic control circuit being formed at least in part inside the first body; and wherein the local antenna is housed inside the first connection region and is connected to the electronic control circuit by the first conductive connection lines.

11. The retinal prosthesis according to claim 1, wherein the electronic stimulation unit comprises a first integrated circuit and a second integrated circuit,
the first integrated circuit comprising a first body of semiconductor material, a first connection region, which is contiguous to the first body and houses first conductive connection lines, and a passivation region, which is contiguous to the first connection region;
the second integrated circuit comprising a second body of semiconductor material and a second connection region, which is contiguous to the second body and houses second conductive connection lines, the first and second integrated circuits being connected by interposition of an insulating region contiguous to the first body and to the second connection region;
the electronic stimulation unit-further comprising a dielectric region contiguous to the passivation region; and
wherein the electronic control circuit comprises a first electronic circuitry, formed at least in part inside the first body, and a second electronic circuitry, formed at least in part inside the second body, the first and second electronic circuitries being electrically connected by means of at least one metal via, which extends through the first body and the insulating region; and
wherein the local antenna is housed inside the dielectric region and is electrically connected to the first electronic circuitry.

12. The retinal prosthesis according to claim 1, wherein the electronic stimulation unit comprises a first integrated circuit and a second integrated circuit,
the first integrated circuit comprising a first body of semiconductor material, a first connection region contiguous to the first body and housing first conductive connection lines, and a passivation region contiguous to the first connection region;
the second integrated circuit comprising a second body of semiconductor material and a second connection region, which is contiguous to the second body and houses second conductive connection lines, the first and second integrated circuits being connected by interposition of an insulating region, contiguous to the first body and to the second connection region; and
wherein the electronic control circuit comprises a first electronic circuitry, formed at least in part inside the first body, and a second electronic circuitry, formed at least in part inside the second body, the first and second electronic circuitries being electrically connected by means of at least one metal via extending through the first body and the insulating region; and
wherein the local antenna is housed inside the first connection region and is electrically connected to the first electronic circuitry.

13. The retinal prosthesis according to claim 1, wherein the electronic stimulation unit further comprises a layer of polymeric material, the electrodes being formed partially within the layer of polymeric material.

14. The retinal prosthesis according to claim 1, wherein the electronic stimulation unit further comprises a package of insulating material, which encloses the electronic control circuit and the local antenna, the electrodes extending at least in part outside the package.

15. The retinal prosthesis according to claim 1, wherein the electronic stimulation unit comprises a magnet configured for constraining the electronic stimulation unit to the electromagnetic expansion.

16. The retinal prosthesis according to claim 1, comprising an external unit including said external antenna, an external transceiver connected to the external antenna, and an image-acquisition device connected to the external transceiver; and wherein the electronic control circuit comprises an internal transceiver, connected to the local antenna.

17. The retinal prosthesis according to claim 1, wherein the first and second expansion antennas are spiral antennas, and wherein the electronic stimulation unit is surrounded at least in part by the second expansion antenna.

18. A retinal prosthesis house-able inside an eye, the prosthesis comprising:
an electronic stimulation unit packaged in a single assembly, the electronic stimulation unit comprising:
a plurality of electrodes configured to stimulate the retina of the eye;
an electronic control unit; and
an integral antenna packaged inside the single assembly of the electronic stimulation unit; and
an electromagnetic expansion comprising a first expansion antenna and a second expansion antenna configured to relay signals from an external antenna to the integral antenna of the electronic stimulation unit such that when the electronic stimulation unit requires replacement, the electromagnetic expansion stays in the eye.

19. The retinal prosthesis of claim 18, wherein the electromagnetic expansion comprises at least one arm hinged to the second expansion antenna about a first axis of rotation.

20. The retinal prosthesis of claim 19, wherein the arm is hinged to the first expansion antenna about a second axis of rotation, and the electromagnetic expansion is elastically displaceable between a resting state, in which the first and second axes of rotation are distinct, and an operative state, in which the first and second axes of rotation coincide.

* * * * *